(12) United States Patent
Lee et al.

(10) Patent No.: US 11,793,862 B2
(45) Date of Patent: Oct. 24, 2023

(54) PHARMACEUTICAL COMPOSITION FOR TREATING NON-ALCOHOLIC FATTY LIVER, NON-ALCOHOLIC STEATOHEPATITIS, OR HEPATIC FIBROSIS USING SSU72 PROTEIN OR A POLYNUCLEOTIDE ENCODING THE SAME

(71) Applicants: CUROGEN TECHNOLOGY CO., LTD., Suwon-si (KR); RESEARCH & BUSINESS FOUNDATION SUNGKYUNKWAN UNIVERSITY, Suwon-si (KR)

(72) Inventors: Chang Woo Lee, Pohang-si (KR); Jin Kwan Lee, Suwon-si (KR); Hyun Soo Kim, Seoul (KR); Ji Hyun Choi, Suwon-si (KR); Se Eun Byeon, Hwaseong-si (KR); Hae In Lee, Suwon-si (KR); Hyeonju Jo, Suwon-si (KR)

(73) Assignee: CUROGEN TECHNOLOGY CO., LTD., Suwon-si (KR)

( * ) Notice: Subject to any disclaimer, the term of this patent is extended or adjusted under 35 U.S.C. 154(b) by 0 days.

(21) Appl. No.: 17/814,594

(22) Filed: Jul. 25, 2022

(65) Prior Publication Data
US 2023/0025176 A1    Jan. 26, 2023

Related U.S. Application Data

(63) Continuation-in-part of application No. PCT/IB2022/050702, filed on Jan. 27, 2022.

(30) Foreign Application Priority Data

Jan. 29, 2021   (KR) .......................... 10-2021-0013620

(51) Int. Cl.
A61K 38/46    (2006.01)
A61K 48/00    (2006.01)
A61P 1/16     (2006.01)

(52) U.S. Cl.
CPC ........ *A61K 38/465* (2013.01); *A61K 48/0008* (2013.01); *A61K 48/0058* (2013.01); *A61P 1/16* (2018.01)

(58) Field of Classification Search
None
See application file for complete search history.

(56) References Cited

U.S. PATENT DOCUMENTS

2018/0140681 A1    5/2018 Cho et al.

FOREIGN PATENT DOCUMENTS

| KR | 20160054719 | 5/2016 |
| KR | 20200010853 | 1/2020 |

OTHER PUBLICATIONS

Kim, et al. (Jan. 2016) "Hepatocyte homeostasis for chromosome ploidization and liver function is regulated by Ssu72 protein phosphatase", Hepatology, 63(1): 247-59. (Year: 2016).*
Chen, et al. (Apr. 16, 2020) "Different Serotypes of Adeno-Associated Virus Vector- and Lentivirus-Mediated Tropism in Choroid Plexus by Intracerebroventricular Delivery", Human Gene Therapy, 31(7-8): 440-47. (Year: 2020).*

* cited by examiner

*Primary Examiner* — Robert M Kelly
(74) *Attorney, Agent, or Firm* — LEX IP MEISTER, PLLC

(57) ABSTRACT

The present invention provides a method for preventing or treating a liver disease selected from the group consisting of non-alcoholic fatty liver, non-alcoholic steatohepatitis and hepatic fibrosis comprising administrating at least one selected from the group consisting of an Ssu72 peptide, a polynucleotide encoding the Ssu72 peptide, and an expression vector comprising the polynucleotide.

24 Claims, 13 Drawing Sheets

Specification includes a Sequence Listing.

Normal diet

MCD diet

MCD diet

MCD diet

Western + Fructose diet (3 months)

CD-HF diet (5weeks)

MCD diet

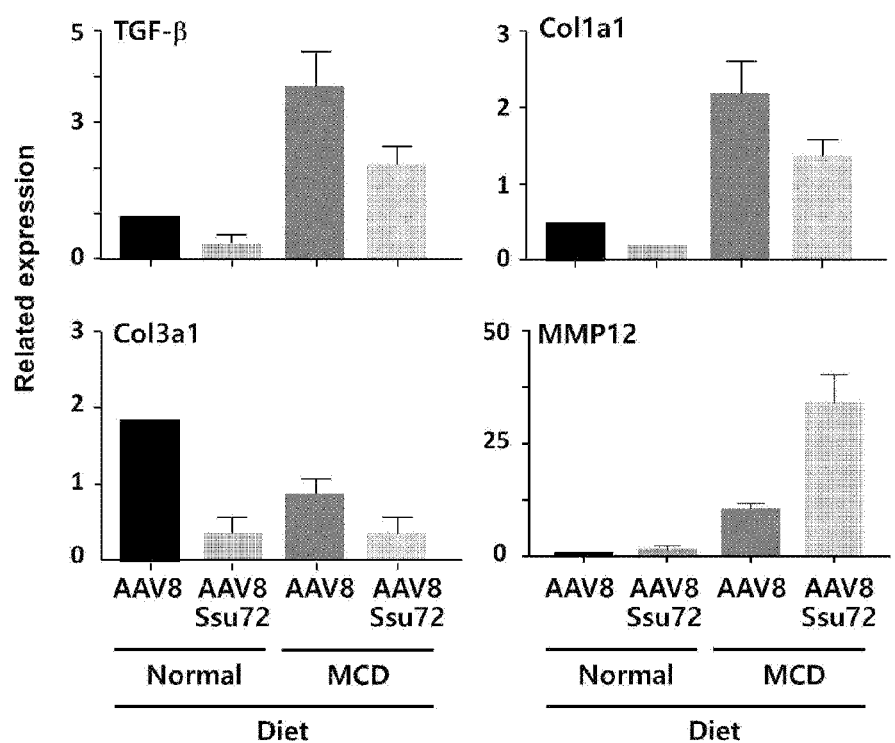

[STAM Model]

[CDAHF Model]

SEQUENCE LISTING

```
Sequence total quantity: 28
SEQ ID NO: 1              moltype = AA    length = 194
FEATURE                   Location/Qualifiers
source                    1..194
                          mol_type = protein
                          organism = Homo sapiens
SEQUENCE: 1
MPSSPLRVAV VCSSNQNRSM EAHNILSKRG FSVRSFGTGT HVKLPGPAPD KPNVYDFKTT    60
YDQMYNDLLR KDKELYTQNG ILHMLDRNKR IKPRPERFQN CKDLFDLILT CEERVYDQVV   120
EDLNSREQET CQPVHVNVD IQDNHEEATL GAFLICELCQ CIQHTEDMEN EIDELLQEFE    180
EKSGRTFLHT VCFY                                                     194

SEQ ID NO: 2              moltype = DNA    length = 585
FEATURE                   Location/Qualifiers
source                    1..585
                          mol_type = genomic DNA
                          organism = Homo sapiens
SEQUENCE: 2
atgccgtcgt ccccgctgcg ggtggcggtg tgtgctcga gcaaccagaa ccggagcatg     60
gaggcgcaca acatcctcag caaacgggga ttcagcgtcc gatcctttgg aacagggact   120
cacgtgaagc ttccaggacc agctcccgac aagcccaatg tttatgattt caaaaccaca   180
tatgaccaga tgtacaatga tcttcttagg aaagacaaag aactctatac acagaatggg   240
attttacata tgctggacag aaataagaga atcaagcccc ggccagaaag attccagaac   300
tgcaaagacc tgtttgatct gatcctcact tgcgaagaga gagtgtatga ccaggtggtg   360
gaagatctga attccagaga acaggagacc tgccagcctg tgcacgtggt caatgtggac   420
atccaggaca accacgagga ggccacctg ggggcgtttc tcatctgtga gctctgccag    480
tgtatccagc acacggaaga catggagaac gagatcgacg agctgctgca ggagttcgag   540
gagaagagtg gccgcacctt tctgcacacc gtctgcttct actga                   585

SEQ ID NO: 3              moltype = DNA    length = 5989
FEATURE                   Location/Qualifiers
misc_feature              1..5989
                          note = pCMV. HA-Ssu72 plasmid
source                    1..5989
                          mol_type = other DNA
                          organism = synthetic construct
SEQUENCE: 3
gacggatcgg gagatctccc gatccctat ggtgcactct cagtacaatc tgctctgatg     60
ccgcatagtt aagccagtat ctgctccctg cttgtgtgtt ggaggtcgct gagtagtgcg   120
cgagcaaaat ttaagctaca acaaggcaag gcttgaccga caattgcata aagaatctgc   180
ttaggttag gcgttttgcg ctgcttcgcg atgtacgggc cagatatacg cgttgacatt    240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta caactccgc cccattgacg caaatgggcg    780
gtaggcgtgt acggtgggag gtctatataa gcagagctct ctggctaact agagaaccca   840
ctgcttactg gcttatcgaa attaatacga ctcactatag ggagacccag cttaccatgg   900
cctaccccta cgacgtgcct gactacgcct ccctcggatc catgccgtcg tccccgctgc   960
gggtggcggt ggtgtgctcg agcaaccaga accggagcat ggaggcgcac aacatcctca  1020
gcaaacgggg attcagcgtc cgatcctttg gaacagggac tcacgtgaag cttccaggac  1080
cagctcccga caagcccaat gtttatgatt tcaaaaccac atatgaccag atgtacaatg  1140
atcttcttag gaaagacaaa gaactctata cacagaatgg gattttacat atgctggaca  1200
gaaataagag aatcaagccc cggccagaaa gattccagaa ctgcaaagac ctgtttgatc  1260
tgatcctcac ttgcgaagag agagtgtatg accaggtggt ggaagatctg aattccagag  1320
aacaggagac ctgccagcct gtgcacgtgg tcaatgtgga catccaggac aaccacgagg  1380
aggccaccct gggggcgttt ctcatctgtg agctctgcca gtgtatccag cacacggaag  1440
acatggagaa cgagatcgac gagctgctgc aggagttcga ggagaagagt ggccgcacct  1500
ttctgcacac cgtctgcttc tactgatcta gagggcccta ttctatagtg tcacctaaat  1560
gctagagctc gctgatcagc ctcgactgtg ccttctagtt gccagccatc tgttgtttgc  1620
ccctccccg tgccttcctt gaccctggaa ggtgccactc ccactgtcct ttcctaataa   1680
aatgaggaaa ttgcatcgca ttgtctgagt aggtgtcatt ctattctggg ggtgggggtg  1740
gggcaggaca gcaagggga ggattgggaa gacaatagca ggcatgctgg ggatgcggtg   1800
ggctctatgg cttctgaggc ggaaagaacc agctggggct ctaggggta tccccacgcg   1860
ccctgtagcg gcgcattaag cgcggcgggt gtggtggtta cgcgcagcgt gaccgctaca  1920
cttgccagcg ccctagcgcc cgctcctttc gctttcttcc cttcctttct cgccacgttc  1980
gccggctttc cccgtcaagc tctaaatcgg ggctccctt tagggttccg atttagtgct   2040
ttacggcacc tcgaccccaa aaacttgat tagggtgatg gttcacgtag tgggccatcg    2100
ccctgatagc cggttttttcg ccctttgacg ttggagtcca cgttctttaa tagtggactc  2160
ttgttccaaa ctggaacaac actcaaccct atctccggtct attctttga tttataaggg  2220
attttgccga tttcggccta ttggttaaaa aatgagctga tttaacaaaa atttaacgcg  2280
aattaattct gtggaatgtg tgtcagttag ggtgtggaaa gtcccaggc tccccagcag   2340
gcagaagtat gcaaagcatg catctcaatt agtcagcaac caggtgtgga aagtcccag   2400
gctccccagc aggcagaagt atgcaaagca tgcatctcaa ttagtcagca accatagtcc  2460
```

```
cgcccctaac tccgcccatc ccgcccctaa ctccgcccag ttccgcccat tctccgcccc   2520
atggctgact aatttttttt atttatgcag aggccgaggc cgcctctgcc tctgagctat   2580
tccagaagta gtgaggaggc ttttttggag gcctaggctt ttgcaaaaag ctcccgggag   2640
cttgtatatc cattttcgga tctgatcaag agacaggatg aggatcgttt cgcatgattg   2700
aacaagatgg attgcacgca ggttctccgg ccgcttgggt ggagaggcta ttcggctatg   2760
actgggcaca acagacaatc ggctgctctg atgccgccgt gttccggctg tcagcgcagg   2820
ggcgcccggt tctttttgtc aagaccgacc tgtccggtgc cctgaatgaa ctgcaggacg   2880
aggcagcgcg gctatcgtgg ctggccacga cgggcgttcc ttgcgcagct gtgctcgacg   2940
ttgtcactga agcgggaagg gactggctgc tattgggcga agtgccgggg caggatctcc   3000
tgtcatctca ccttgctcct gccgagaaag tatccatcat ggctgatgca atgcggcggc   3060
tgcatacgct tgatccggct acctgcccat tcgaccacca agcgaaacat cgcatcgagc   3120
gagcacgtac tcggatggaa gccggtcttg tcgatcagga tgatctggac gaagagcatc   3180
aggggctcgc gccagccgaa ctgttcgcca ggctcaaggc gcgcatgccc gacggcgagg   3240
atctcgtcgt gacccatggc gatgctgctt gccgaatatc atggtggaa aatggccgct   3300
tttctggatt catcgactgt ggccggctgg gtgtggcgga ccgctatcag gacatagcgt   3360
tggctacccg tgatattgct gaagagcttg gcggcgaatg ggctgaccgc ttcctcgtgc   3420
tttacggtat cgccgctccc gattcgcagc gcatcgcctt ctatcgcctt cttgacgagt   3480
tcttctgagc gggactctgg ggttcgaaat gaccgaccaa gcgacgccca acctgccatc   3540
acgagatttc gattccaccg ccgccttcta tgaaaggttg gcttcggaa tcgttttccg   3600
ggacgccggc tggatgatcc tccagcgcgg ggatctcatg ctggagttct tcgcccaccc   3660
caacttgttt attgcagctt ataatggtta caaataaagc aatagcatca caaatttcac   3720
aaataaagca tttttttcac tgcattctag ttgtggtttg tccaaactca tcaatgtatc   3780
ttatcatgtc tgtataccgt cgacctctag ctagagcttg gcgtaatcat ggtcatagct   3840
gtttcctgtg tgaaattgtt atccgctcac aattccacac aacatacgag ccggaagcat   3900
aaagtgtaaa gcctggggtg cctaatgagt gagctaactc acattaattg cgttgcgctc   3960
actgcccgct ttccagtcgg gaaacctgtc gtgccagctg cattaatgaa tcggccaacg   4020
cgcggggaga ggcggtttgc gtattgggcg ctcttccgct tcctcgctca ctgactcgct   4080
gcgctcggtc gttcggctgc ggcgagcgg atcagctcac tcaaaggcgg taatacggtt   4140
atccacagaa tcaggggata acgcaggaaa gaacatgtga gcaaaaggcc agcaaaaggc   4200
caggaaccgt aaaaaggccg cgttgctggc gtttttccat aggctccgcc ccctgacga   4260
gcatcacaaa aatcgacgct caagtcagag gtggcgaaac ccgacaggac tataaagata   4320
ccaggcgttt ccccctggaa gctccctcgt gcgctctcct gttccgaccc tgccgcttac   4380
cggatacctg tccgcctttc tcccttcggg aagcgtggcg ctttctcata gctcacgctg   4440
taggtatctc agttcggtgt aggtcgttcg ctccaagctg ggctgtgtgc acgaaccccc   4500
cgttcagccc gaccgctgcg ccttatccgg taactatcgt cttgagtcca acccggtaag   4560
acacgactta tcgccactgg cagcagccac tggtaacagg attagcagag cgaggtatgt   4620
aggcggtgct acagagttct tgaagtggtg gcctaactac ggctacacta agaacagt   4680
atttggtatc tgcgctctgc tgaagccagt taccttcgga aaaagagttg gtagctcttg   4740
atccggcaaa caaaccaccg ctggtagcgg tggtttttta gtttgcaagc agcagattac   4800
gcgcagaaaa aaaggatctc aagaagatcc tttgatcttt tctacggggt ctgacgctca   4860
gtggaacgaa aactcacgtt aagggatttt ggtcatgaga ttatcaaaaa ggatcttcac   4920
ctagatcctt ttaaattaaa aatgaagttt taaatcaatc taaagtatat atgagtaaac   4980
ttggtctgac agttaccaat gcttaatcag tgaggcacct atctcagcga tctgtctatt   5040
tcgttcatcc atagttgcct gactccccgt cgtgtagata actacgatac gggagggctt   5100
accatctggc cccagtgctg caatgatacc gcgagaccca cgctcaccgg ctccagattt   5160
atcagcaata aaccagccag ccggaagggc cgagcgcaga agtggtcctg caactttatc   5220
cgcctccatc cagtctatta attgttgccg ggaagctaga gtaagtagt cgccagttaa   5280
tagtttcgc aacgttgttg ccattgctac aggcatcgtg gtgtcacgct cgtcgtttgg   5340
tatggcttca ttcagctccg gttcccaacg atcaaggcga gttacatgat cccccatgtt   5400
gtgcaaaaaa gcggttagct ccttcggtcc tccgatcgtt gtcagaagta agttggccgc   5460
agtgttatca ctcatggtta tggcagcact gcataattct cttactgtca tgccatccgt   5520
aagatgcttt tctgtgactg gtgagtactc aaccaagtca ttctgagaat agtgtatgcg   5580
gcgaccgagt tgctcttgcc cggcgtcaat acgggataat accgcgccac atagcagaac   5640
tttaaaagtg ctcatcattg gaaaacgttc tcggggcga aaactctcaa ggatcttacc   5700
gctgttgaga tccagttcga tgtaacccac tcgtgcaccc aactgatctt cagcatcttt   5760
tactttcacc agcgtttctg ggtgagcaaa aacaggaagg caaaatgccg caaaaaaggg   5820
aataagggcg acacggaaat gttgaatact catactcttc ctttttcaat attattgaag   5880
catttatcag ggttattgtc tcatgagcgg atacatattt gaatgtattt agaaaaataa   5940
acaaataggg gttccgcgca catttccccg aaaagtgcca cctgacgtc                 5989

SEQ ID NO: 4           moltype = DNA   length = 6456
FEATURE                Location/Qualifiers
misc_feature           1..6456
                       note = AAV8.TBG.HA-Ssu72
source                 1..6456
                       mol_type = other DNA
                       organism = synthetic construct
SEQUENCE: 4
ctgcgcgctc gctcgctcac tgaggccgcc cggcaaagc ccgggcgtcg ggcgaccttt      60
ggtcgcccgg cctcagtgag cgagcgagcg cgcagagagg gagtggccaa ctccatcact    120
aggggttcct gtgtagttaat gattaacccg ccatgctact tatctaccag ggtaatgggg   180
atcctctaga actatagcta gaattcgccc ttaagctagc aggttaattt ttaaaaagca    240
gtcaaaagtc caagtggccc ttggcagcat ttactctctc tgtttgctct ggttaataat    300
ctcaggagca caaacattcc agatccaggt taattttaa aaagcagtca aaagtccaa      360
tggcccttgg cagcatttac tctctctgtt tgctctggtt aataatctca ggagcacaaa    420
cattccagat ccggcgcgcc agggctggaa gctacctttg acatcattc ctctgcgaat     480
gcatgtataa tttctacaga acctattaga aaggatcacc cagcctctgc ttttgtacaa    540
cttttccctta aaaaactgcc aattccactg ctgtttggcc caatagtgag aacttttcc    600
tgctgcctct tggtgctttt gcctatggcc cctattctgc ctgctgaaga cactcttgcc    660
```

```
agcatggact taaacccctc cagctctgac aatcctcttt ctcttttgtt ttacatgaag   720
ggtctggcag ccaaagcaat cactcaaagt tcaaaccttg tcattttttg ctttgttcct   780
cttggccttg gttttgtaca tcagctttga aaataccatc ccagggttaa tgctggggtt   840
aatttataac taagagtgct ctagttttgc aatacaggac atgctataaa aatggaaaga   900
tgttgctttc tgagagacag cttttattgcg gtagtttatc acagttaaat tgctaacgca   960
gtcagtgctt ctgacacaac agtctcgaac ttaagctgca gaagttggtc gtgaggcact  1020
gggcaggtaa gtatcaaggt tacaagacag gtttaaggag accaatagaa actgggcttg  1080
tcgagacaga gaagactctt gcgtttctga taggcaccta ttggtcttac tgacatccac  1140
tttgccttc tctccacagg tgtccactcc cagttcaatt acagctctta aggctagagt  1200
acttaatacg actcactata ggctagcacc atggaattct tttacccata cgatgttcct  1260
gactatgcgg gctatcccta tgacgtcccg gactatgcag gatccatgcc gtcgtccccg  1320
ctgcgggtgg cggtggtgtg ctcgagcaac cagaaccgga gcatggaggc gcacaacatc  1380
ctcagcaaac ggggattcag cgtccgatcc tttggaacag ggactcacgt gaagcttcca  1440
ggaccagctc ccgacaagcc caatgtttat gatttcaatg ccacatatga ccagatgtac  1500
aatgatcttc ttaggaaaga caaagaactc tatacacaga atgggatttt acatatgctg  1560
gacagaaata agagaatcaa gccccggcca gaaagattcc agaactgcaa agacctgttt  1620
gatctgatcc tcacttgcga agagagagtg tatgaccagg tggtgaaga tctgaattcc  1680
agagaacagg agacctgcca gcctgtgcac gtggtcaatg tggacatcca ggacaaccac  1740
gaggaggcca ccctgggggc gtttctcatc tgtgagctct gccagtgtat ccagcacacg  1800
gaagacatgg agaacgagat cgacgagctg ctgcaggagt tcgaggagaa gagtggccgc  1860
acctttctgc acaccgtctg cttctactga ggtacccgct cgaggttaac gaattccgcc  1920
cccccccccc ccccccccct ctccctcccc cccccctaac gttactggcc gaagccgctt  1980
ggaataaggc cggtgtgcgt ttgtctatat gttattttcc accatattgc cgtcttttgg  2040
caatgtgagg gcccggaaac ctggccctgt cttcttgacg agcattccta ggggtctttc  2100
ccctctcgcc aaaggaatgc aaggtctgtt gaatgtcgtg aaggaagcag ttcctctgga  2160
agcttcttga agacaaacaa cgtctgtagc gacccttgt aggcagcgga accccccac  2220
tggcgacagg tgcctctgcg gccaaaagcc acgtgtataa gatacacctg caaaggcggc  2280
acaaccccag tgccacgttg tgagttggat agttgtggaa agagtcaaat ggctctcctc  2340
aagcgtattc aacaagggc tgaaggatgc ccagaaggta cccattgta tgggatctga  2400
tctggggcct cggtgcacat gctttacatg tgtttagtcg aggttaaaaa aacgtctagg  2460
ccccccgaac cacggggacg tggtttttcct ttgaaaaaca cgatgataat atggccacaa  2520
ccatggtgag caagggcgag gagctgttca cggggtggt gcccatcctg gtcgagctgg  2580
acggcgacgt aaacggccac aagttcagcg tgtctggcga gggcgagggc gatgccacct  2640
acggcaagct gaccctgaag ttcatctgca ccaccggcaa gctgcccgtg ccctggccca  2700
ccctcgtgac caccctgacc tacggcgtgc agtgcttcag ccgctacccc gaccacatga  2760
agcagcacga cttcttcaag tccgccatgc ccgaaggcta cgtccaggag cgcaccatct  2820
tcttcaagga cgacggcaac tacaagaccc gcgccgaggt gaagttcgag ggcgacaccc  2880
tggtgaaccg catcgagctg aagggcatcg acttcaagga ggacggcaac atcctggggc  2940
acaagctgga gtacaactac aacagccaca acgtctatat catggccgac aagcagaaga  3000
acggcatcaa ggcgaacttc aagatccgcc acaacatcga ggacggcagc gtgcagctcg  3060
ccgaccacta ccagcagaac acccccatcg gcgacggccc cgtgctgctg cccgacaacc  3120
actacctgag cacccagtcc gccctgagca agaccccaa cgagaagcgc gatcacatgg  3180
tcctgctgga gttcgtgacc gccgccggga tcactctgga cgtgtacaagt  3240
aagtcgaccc gggcggcctc gaggacgggg tgaactacgc ctgaggatcc gatctttttc  3300
cctctgccaa aaattatggg gacatcatga agccccttga gcatctgact ctggcaat  3360
aaaggaaatt tattttcatt gcaatagtgt gttggaatt tttgtgtctc tcactcggaa  3420
gcaattcgtt gatctgaatt tcgaccaccc ataatccca ttaccctgg agataagtag  3480
catgcgggt taatcattaa ctacaaggaa cccctagtga tggagttggc cactccctct  3540
ctgcgcgctc gctcgctcac tgaggccggg cgaccaaagg tcgcccgacg cccgggcttt  3600
gcccggggcgg cctcagtgag cgagcgagcg cgcagcctta ttaacctaa ttcactggcc  3660
gtcgttttac aacgtcgtga ctgggaaaac cctggcgtta cccaacttaa tcgccttgca  3720
gcacatcccc ctttcgccag ctggcgtaat agcgaagagg cccgcaccga tcgcccttcc  3780
caacagttgc gcagcctgaa tggcgaatgg gacgcgccct gtagcggcgc attaagcgcg  3840
gcgggtgtgg tggttacgcg cagcgtgacc gctacacttg ccagcgccct agcgcccgct  3900
cctttcgctt tcttcccttc cttttctcgcc acgttcgccg gctttccccg tcaagctcta  3960
aatcggggc tccctttagg gttccgattt agtgctttac ggcacctcga ccccaaaaaa  4020
cttgattagg gtgatggttc acgtagtggg ccatcgccct gatagacggt ttttcgccct  4080
ttgacgttgg agtccacgtt ctttaatagt ggactcttgt tccaaactgg aacaacactc  4140
aaccctatct cggtctattc ttttgattta taagggatttc tgccgatttc ggcctattgg  4200
ttaaaaaatg agctgattta acaaaaattt aacgcgaatt ttaacaaaat attaacgctt  4260
acaatttagg tggcactttt cggggaaatg tgcgcggaac ccctatttgt ttatttttct  4320
aaatacattc aaatatgtat ccgctcatga gacaataacc ctgataaatg cttcaataat  4380
attgaaaaag gaagagtatg agtattcaac atttccgtgt cgcccttatt cccttttttg  4440
cggcattttg ccttcctgtt tttgctcacc cagaaacgct ggtgaaagta aaagatgctg  4500
aagatcagtt gggtgcacga gtgggttaca tcgaactgga tctcaacagc ggtaagatcc  4560
ttgagagttt tcgccccgaa gaacgttttc caatgatgag cacttttaaa gttctgctat  4620
gtggcgcggt attatcccgt attgacgccg ggcaagagca actcggtcgc cgcatacact  4680
attctcagaa tgacttggtt gagtactcac cagtcacaga aaagcatctt acggatggca  4740
tgacagtaag agaattatgc agtgctgcca taaccatgag tgataacact gcggccaact  4800
tacttctgac aacgatcgga ggaccgaagg agctaaccgc ttttttgcac aacatggggg  4860
atcatgtaac tcgccttgat cgttgggaac cggagctgaa tgaagccata ccaaacgacg  4920
agcgtgacac cacgatgcct gtagcaatgg caacaacgtt gcgcaaacta ttaactggcg  4980
aactacttac tctagcttcc cggcaacaat taatagactg gatggaggcg gataaagttg  5040
caggaccact tctgcgctcg gcccttccgg ctggctggtt tattgctgat aaatctggag  5100
ccggtgagcg tgggtctcgc ggtatcattg cagcactggg gccagatggt aagccctccc  5160
gtatcgtagt tatctacacg acggggagtc aggcaactat ggatgaacga aatagacaga  5220
tcgctgagat aggtgcctca ctgattaagc attggtaact gtcagaccaa gtttactcat  5280
atatacttta gattgattta aaacttcatt tttaatttaa aaggatctag gtgaagatcc  5340
tttttgataa tctcatgacc aaaatccctt aacgtgagtt ttcgttccac tgagcgtcag  5400
```

-continued

```
acccgtaga    aaagatcaaa    ggatcttctt    gagatccttt    ttttctgcgc    gtaatctgct    5460
gcttgcaaac   aaaaaaacca    ccgctaccag    cggtggtttg    tttgccggat    caagagctac    5520
caactctttt   tccgaaggta    actggcttca    gcagagcgca    gataccaaat    actgttcttc    5580
tagtgtagcc   gtagttaggc    caccacttca    agaactctgt    agcaccgcct    acatacctcg    5640
ctctgctaat   cctgttacca    gtggctgctg    ccagtggcga    taagtcgtgt    cttaccgggt    5700
tggactcaag   acgatagtta    ccggataagg    cgcagcggtc    gggctgaacg    ggggggttcgt   5760
gcacacagcc   cagcttggag    cgaacgacct    acaccgaact    gagataccta    cagcgtgagc    5820
tatgagaaag   cgccacgctt    cccgaaggga    gaaaggcgga    caggtatccg    gtaagcggca    5880
gggtcggaac   aggagagcgc    acgagggagc    ttccaggggg    aaacgcctgg    tatctttata    5940
gtcctgtcgg   gtttcgccac    ctctgacttg    agcgtcgatt    tttgtgatgc    tcgtcagggg    6000
ggcggagcct   atgaaaaac    gccagcaacg    cggcctttt    acggttcctg    gccttttgct    6060
ggcctttgc    tcacatgttc    tttcctgcgt    tatccctga    ttctgtggat    aaccgtatta    6120
ccgcctttga   gtgagctgat    accgctcgcc    gcagccgaac    gaccgagcgc    agcgagtcag    6180
tgagcgagga   agcggaagag    cgcccaatac    gcaaaccgcc    tctccccgcg    cgttggccga    6240
ttcattaatg   cagctggcac    gacaggttc    ccgactggaa    agcgggcagt    gagcgcaacg    6300
caattaatgt   gagttagctc    actcattagg    caccccaggc    tttacacttt    atgcttccgg    6360
ctcgtatgtt   gtgtggaatt    gtgagcggat    aacaatttca    cacaggaaac    agctatgacc    6420
atgattacgc   cagatttaat    taaggcctta    attagg                                  6456

SEQ ID NO: 5            moltype = DNA   length = 19
FEATURE                 Location/Qualifiers
misc_feature            1..19
                        note = TGF-beta forward primer
source                  1..19
                        mol_type = other DNA
                        organism = synthetic construct
SEQUENCE: 5
caccggagag ccctggata                                                              19

SEQ ID NO: 6            moltype = DNA   length = 19
FEATURE                 Location/Qualifiers
misc_feature            1..19
                        note = TGF-beta reverse primer
source                  1..19
                        mol_type = other DNA
                        organism = synthetic construct
SEQUENCE: 6
caccggagag ccctggata                                                              19

SEQ ID NO: 7            moltype = DNA   length = 25
FEATURE                 Location/Qualifiers
misc_feature            1..25
                        note = Col1a1 forward primer
source                  1..25
                        mol_type = other DNA
                        organism = synthetic construct
SEQUENCE: 7
gggtctagac atgttcagct ttgtg                                                       25

SEQ ID NO: 8            moltype = DNA   length = 22
FEATURE                 Location/Qualifiers
misc_feature            1..22
                        note = Col1a1 reverse primer
source                  1..22
                        mol_type = other DNA
                        organism = synthetic construct
SEQUENCE: 8
acccttaggc cattgtgtat gc                                                          22

SEQ ID NO: 9            moltype = DNA   length = 20
FEATURE                 Location/Qualifiers
misc_feature            1..20
                        note = Fasn forward primer
source                  1..20
                        mol_type = other DNA
                        organism = synthetic construct
SEQUENCE: 9
attgcatcaa gcaagtgcag                                                             20

SEQ ID NO: 10           moltype = DNA   length = 19
FEATURE                 Location/Qualifiers
misc_feature            1..19
                        note = Fasn reverse primer
source                  1..19
                        mol_type = other DNA
                        organism = synthetic construct
SEQUENCE: 10
gagccgtcaa acaggaaag                                                              19
```

```
SEQ ID NO: 11              moltype = DNA  length = 19
FEATURE                    Location/Qualifiers
misc_feature               1..19
                           note = Srebp1c forward primer
source                     1..19
                           mol_type = other DNA
                           organism = synthetic construct
SEQUENCE: 11
ggcttgtcct ttgggaagc                                                  19

SEQ ID NO: 12              moltype = DNA  length = 18
FEATURE                    Location/Qualifiers
misc_feature               1..18
                           note = Srebp1c reverse primer
source                     1..18
                           mol_type = other DNA
                           organism = synthetic construct
SEQUENCE: 12
cgcctatgct ggtgcaca                                                   18

SEQ ID NO: 13              moltype = DNA  length = 20
FEATURE                    Location/Qualifiers
misc_feature               1..20
                           note = ACC1 forward primer
source                     1..20
                           mol_type = other DNA
                           organism = synthetic construct
SEQUENCE: 13
ccaggccatg ttgagacgct                                                 20

SEQ ID NO: 14              moltype = DNA  length = 20
FEATURE                    Location/Qualifiers
misc_feature               1..20
                           note = ACC1 reverse primer
source                     1..20
                           mol_type = other DNA
                           organism = synthetic construct
SEQUENCE: 14
ccagccagcc tcttgactat                                                 20

SEQ ID NO: 15              moltype = DNA  length = 22
FEATURE                    Location/Qualifiers
misc_feature               1..22
                           note = PPARa forward primer
source                     1..22
                           mol_type = other DNA
                           organism = synthetic construct
SEQUENCE: 15
ggatgtcaca caatgcaatt cg                                              22

SEQ ID NO: 16              moltype = DNA  length = 22
FEATURE                    Location/Qualifiers
misc_feature               1..22
                           note = PPARa reverse primer
source                     1..22
                           mol_type = other DNA
                           organism = synthetic construct
SEQUENCE: 16
tcacagaacg gcttcctcag gt                                              22

SEQ ID NO: 17              moltype = DNA  length = 19
FEATURE                    Location/Qualifiers
misc_feature               1..19
                           note = Pgc1a forward primer
source                     1..19
                           mol_type = other DNA
                           organism = synthetic construct
SEQUENCE: 17
ccctgccatt gttaagacc                                                  19

SEQ ID NO: 18              moltype = DNA  length = 19
FEATURE                    Location/Qualifiers
misc_feature               1..19
                           note = Pgc1a reverse primer
source                     1..19
                           mol_type = other DNA
                           organism = synthetic construct
SEQUENCE: 18
tgctgctgtt cctgttttc                                                  19
```

-continued

```
SEQ ID NO: 19              moltype = DNA  length = 20
FEATURE                    Location/Qualifiers
misc_feature               1..20
                           note = Col3a1 forward primer
source                     1..20
                           mol_type = other DNA
                           organism = synthetic construct
SEQUENCE: 19
tacacctgct cctgtgcttc                                                   20

SEQ ID NO: 20              moltype = DNA  length = 20
FEATURE                    Location/Qualifiers
misc_feature               1..20
                           note = Col3a1 reverse primer
source                     1..20
                           mol_type = other DNA
                           organism = synthetic construct
SEQUENCE: 20
cattcctccc actccagact                                                   20

SEQ ID NO: 21              moltype = DNA  length = 19
FEATURE                    Location/Qualifiers
misc_feature               1..19
                           note = MMP12 forward primer
source                     1..19
                           mol_type = other DNA
                           organism = synthetic construct
SEQUENCE: 21
accagagcca cactatccc                                                    19

SEQ ID NO: 22              moltype = DNA  length = 20
FEATURE                    Location/Qualifiers
misc_feature               1..20
                           note = MMP12 reverse primer
source                     1..20
                           mol_type = other DNA
                           organism = synthetic construct
SEQUENCE: 22
ctcctgcctc acatcatacc                                                   20

SEQ ID NO: 23              moltype = DNA  length = 19
FEATURE                    Location/Qualifiers
misc_feature               1..19
                           note = MMP13 forward primer
source                     1..19
                           mol_type = other DNA
                           organism = synthetic construct
SEQUENCE: 23
ctggcacacg cttttcctc                                                    19

SEQ ID NO: 24              moltype = DNA  length = 22
FEATURE                    Location/Qualifiers
misc_feature               1..22
                           note = MMP13 reverse primer
source                     1..22
                           mol_type = other DNA
                           organism = synthetic construct
SEQUENCE: 24
atgggcagca acaataaaca ag                                                22

SEQ ID NO: 25              moltype = DNA  length = 20
FEATURE                    Location/Qualifiers
misc_feature               1..20
                           note = SMA forward primer
source                     1..20
                           mol_type = other DNA
                           organism = synthetic construct
SEQUENCE: 25
ctgacagagg caccactgaa                                                   20

SEQ ID NO: 26              moltype = DNA  length = 20
FEATURE                    Location/Qualifiers
misc_feature               1..20
                           note = SMA reverse primer
source                     1..20
                           mol_type = other DNA
                           organism = synthetic construct
SEQUENCE: 26
```

```
catctccaga gtccagcaca                                                        20

SEQ ID NO: 27            moltype = DNA  length = 22
FEATURE                  Location/Qualifiers
misc_feature             1..22
                         note = Timp forward primer
source                   1..22
                         mol_type = other DNA
                         organism = synthetic construct
SEQUENCE: 27
ctcaaagacc tatagtgctg gc                                                     22

SEQ ID NO: 28            moltype = DNA  length = 20
FEATURE                  Location/Qualifiers
misc_feature             1..20
                         note = Timp reverse primer
source                   1..20
                         mol_type = other DNA
                         organism = synthetic construct
SEQUENCE: 28
caaagtgacg gctctggtag                                                        20
```

PHARMACEUTICAL COMPOSITION FOR TREATING NON-ALCOHOLIC FATTY LIVER, NON-ALCOHOLIC STEATOHEPATITIS, OR HEPATIC FIBROSIS USING SSU72 PROTEIN OR A POLYNUCLEOTIDE ENCODING THE SAME

CROSS REFERENCE TO RELATED APPLICATIONS

This application claims priority to Korean Patent Application No. 2021-0013620 filed on Jan. 29, 2021. In addition, this application is a continuation-in-part of an International Patent Application No. PCT/IB2022/050702 filed on Jan. 27, 2022. Both of the above applications are incorporated herein by reference in their entirety.

REFERENCE TO AN ELECTRONIC SEQUENCE LISTING

The contents of the electronic sequence listing (SPJ20225255US_sequence_listing.xml; Size: 48 K bytes; and Date of Creation: Jul. 25, 2022) is herein incorporated by reference in its entirety. The contents of the electronic sequence listing in no way introduces new matter into the specification.

TECHNICAL FIELD

The present invention relates to a pharmaceutical composition or a method for preventing or treating fatty liver, steatohepatitis, hepatic fibrosis, more particularly relates to a pharmaceutical composition for preventing or treating non-alcoholic fatty liver, non-alcoholic steatohepatitis, hepatic fibrosis using an Ssu72 peptide or a polynucleotide encoding the same.

BACKGROUND ART

Obesity is increasing to the same level as past infectious diseases worldwide in the $21^{st}$ century. Modern peoples' excessive nutrition and sedentary lifestyle patterns are causes of various metabolic syndrome, including obesity, and due to various drugs and stress in addition to the above causes, the number of people diagnosed with chronic liver diseases such as chronic fatty liver and steatohepatitis is rapidly increasing. Chronic fatty liver and steatohepatitis spans the range of simple steatosis to non-alcoholic steatohepatitis and alcoholic steatohepatitis accompanied by inflammation and fibrosis, and these symptoms are thought to be the cause of cirrhosis and liver failure, and furthermore, liver cancer. It is known that the non-alcoholic steatohepatitis is caused by worsening various symptoms such as hepatocellular necrosis, adiposis, lipotoxicity, and hepatitis caused by liver damage. In particular, non-alcoholic steatohepatitis is a complex disease accompanied by apoptosis of hepatocytes, invasion of various chronic inflammatory immune cells, proliferation and fibrosis of activated hepatic stellate cells, and no drug was approved currently and few of clinically tested drugs is evaluated as effective. Therefore, there is an urgent need to develop new therapeutics that have no side effects, economical in cost, and have very excellent therapuetic effects in the future. In this regard, Korean Patent Publication No. 2020-0010853 discloses a pharmaceutical composition for the prevention or treatment of non-alcoholic steatohepatitis.

SUMMARY OF THE INVENTION

However, in the case of the prior art, there is a problem in that therapeutic efficiency is not high along with side effects such as chronic hepatitis and cirrhosis.

The present invention aims to solve various problems including the above problems, and provides a pharmaceutical composition capable of effectively treating non-alcoholic fatty liver, non-alcoholic steatohepatitis, or hepatic fibrosis without side effects with high sensitivity and specificity. However, these problems are exemplary, and the scope of the present invention is not limited thereto.

In an aspect of the present invention, there is provided a method for treating a patient suffering from a liver disease selected from the group consisting of non-alcoholic fatty liver, non-alcoholic steatohepatitis and hepatic fibrosis comprising administrating at least one selected from the group consisting of to the patient:

an Ssu72 peptide, a polynucleotide encoding the Ssu72 peptide, and an expression vector comprising the polynucleotide.

In an aspect of the present invention, there is provided a method for treating a liver disease selected from a group consisting of non-alcoholic fatty liver, non-alcoholic steatohepatitis and hepatic fibrosis in a subject comprising:

measuring the expression level or activity of the Ssu72 peptide in a sample obtained from the subject; and administrating at least one selected from the group consisting of i) to iii) to the subject when the expression level of the Ssu72 peptide in the subject is lower than that of normal subjects or the Ssu72 peptide is expressed in an inactive form;

i) an Ssu72 peptide having an amino acid sequence represented by SEQ ID NO: 1, ii) a polynucleotide encoding the Ssu72 peptide, and iii) an expression vector containing the polynucleotide.

In another aspect of the present invention, provided are a method for preventing a liver disease selected from the group consisting of non-alcoholic fatty liver, non-alcoholic steatohepatitis and hepatic fibrosis in a subject need thereof, comprising administering at least one selected from the group consisting of i) to iii) to the subject:

i) an Ssu72 peptide having an amino acid sequence represented by SEQ ID NO: 1, ii) a polynucleotide encoding the Ssu72 peptide, and iii) an expression vector containing the polynucleotide.

In another aspect of the present invention, there is provided a method for diagnosing non-alcoholic steatohepatotistis in a patient suffering from hepatotitis comprising:

measuring the expression level or activity of an Ssu72 peptide in samples obtained from the patient; and diagnosing the patient as one having non-alcoholic steatohepatitis when the expression level of the Ssu72 peptide in the patient is lower than that of normal subjects or the Ssu72 peptide is expressed in an inactive form in the patient.

In another aspect of the present invention, there is provided a method for diagnosing non-alcoholic steatohepatitis in a patient suffering from a liver disease comprising:

measuring the expression level or activity of an Ssu72 peptide in a sample obtained from the patient; and diagnosing the patient as one having non-alcoholic steatohepatitis when the expression level of the Ssu72 peptide in the patient is lower than that of normal subjects or the Ssu72 peptide is expressed in an inactive form in the patient.

In another aspect of the present invention, there is provided a pharmaceutical composition for treating liver disease selected from the group consisting of non-alcoholic fatty liver, non-alcoholic steatohepatitis, and liver cirrhosis comprising at least one selected from the group consisting of:

i) an Ssu72 peptide having an amino acid sequence represented by SEQ ID NO: 1, ii) a polynucleotide encoding the Ssu72 peptide, and iii) an expression vector containing the polynucleotide.

In an aspect of the present invention, there is provided a pharmaceutical composition for preventing liver disease selected from the group consisting of non-alcoholic fatty liver, non-alcoholic steatohepatitis, and liver cirrhosis comprising at least one selected from the group consisting of:

i) an Ssu72 peptide having an amino acid sequence represented by SEQ ID NO: 1, ii) a polynucleotide encoding the Ssu72 peptide, and iii) an expression vector containing the polynucleotide.

In another aspect of the present invention, there is provided use of i) an Ssu72 peptide having an amino acid sequence represented by SEQ ID NO: 1, ii) a polynucleotide encoding the Ssu72 peptide, or iii) an expression vector containing the polynucleotide in the manufacture of a medicament for alleviating or treating liver disease selected from the group consisting of non-alcoholic fatty liver, non-alcoholic steatohepatitis, and liver cirrhosis.

Advantageous Effects

As described above, when the pharmaceutical composition for preventing or treating liver disease comprising the Ssu72 peptide or a polynucleotide encoding the same according to an embodiment of the present invention is expressed in the liver, it is possible to effectively inhibit the lipogenesis activity of hepatocytes and, the expression and secretion of TGF-β and inhibit the activation and fibrosis of hepatic stellate cells thereby, so it can be used as a therapeutic agent for preventing or treating liver diseases including non-alcoholic fatty liver, nonalcoholic steatohepatitis and liver fibrosis. Of course, the scope of the present invention is not limited by these effects.

BRIEF DESCRIPTIONS OF DRAWINGS

FIG. 1 is a schematic diagram illustrating the structure of pCMV.HA-Ssu72 vector as a non-viral vector according to an embodiment of the present invention used in the example of the present invention.

FIG. 2 is a schematic diagram representing procedure of preparing AAV8.TBG.HA-Ssu72 vector as a viral vector according to an embodiment of the present invention and strategies to package recombinant adeno-associated viruses (AAVs) expressing Ssu72 peptide driven by the Thyroxine-binding globulin (TBG) promoter according to an embodiment of the present invention. TBG promoter described in FIG. 2 was used for liver-specific expression of The Ssu72 peptide in the AAV viral vector. The AAV8.TBG.HA-Ssu72 virus can be referred to as "AAV8 Ssu72" in the detailed description and drawings for convenience.

Figure 4A:
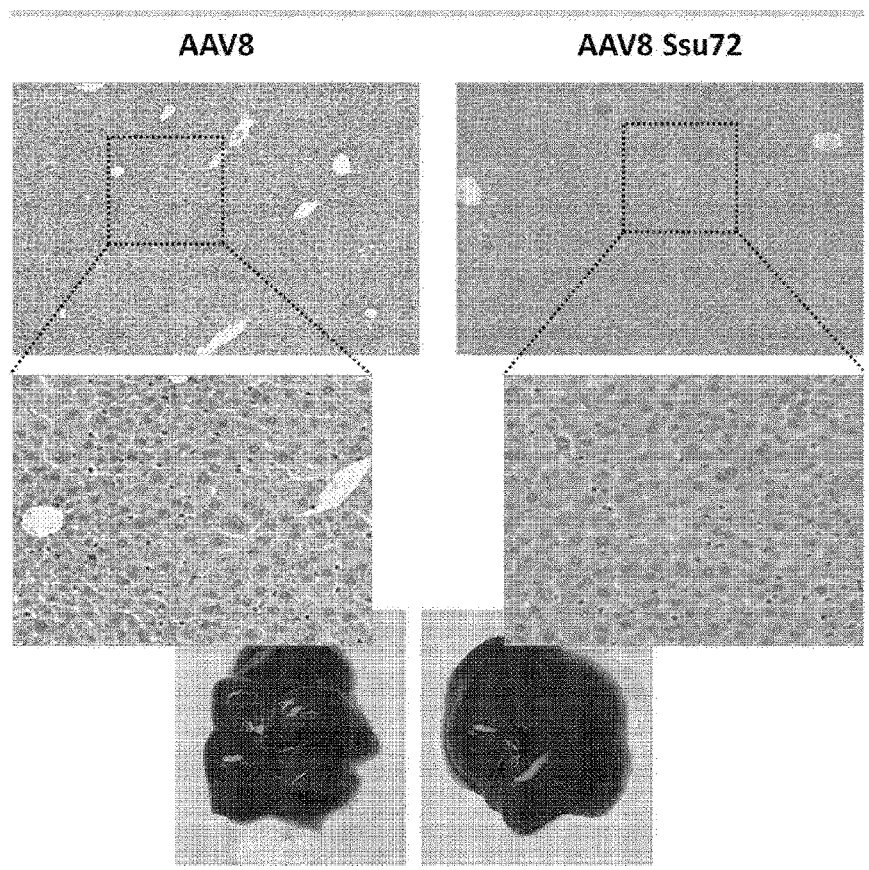
FIG. 4A shows a series of photographs of overall appearances of livers excised from experimental animals (bottom) and a series of microscopic photographs of H&E stained liver tissue sections from the experimental animals (top), representing the result of evaluating side effects according to the injection of AAV8 Ssu72 virus after applying normal diet to experimental mice.
Figure 4B:
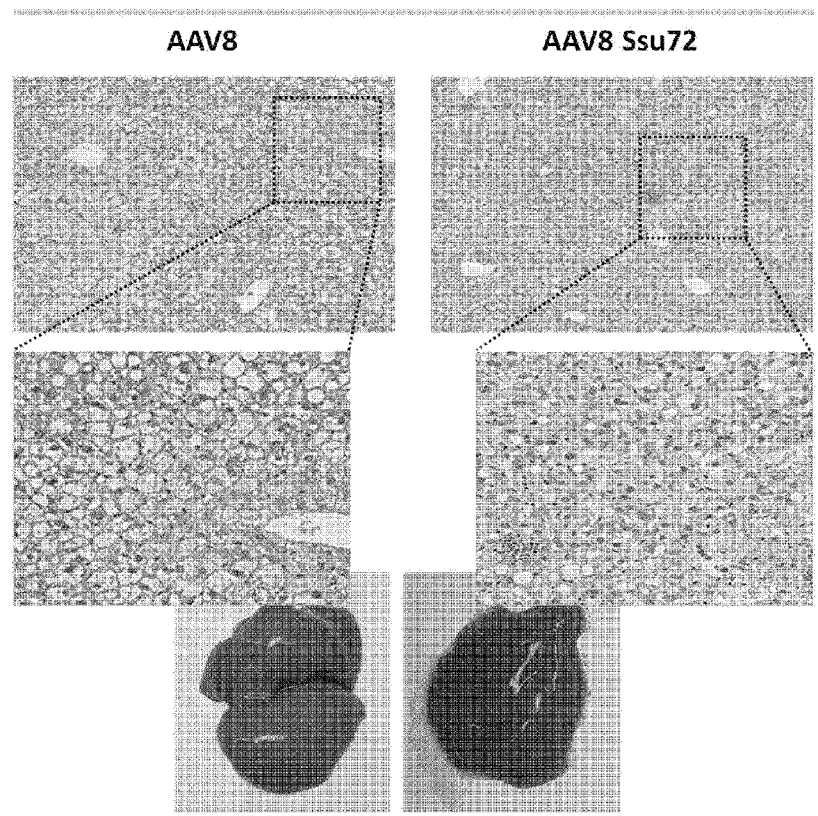

FIG. 4B shows a series of photographs of overall appearances of livers excised from experimental animals (bottom) and a series of microscopic photographs of H&E stained liver tissue sections from the experimental animals (top), representing the result of evaluating side effects according to the injection of AAV8 Ssu72 virus after applying non-alcoholic steatohepatitis-inducing diet (Methionine and choline-deficient diet, MCD) to experimental mice.

Figure 5A:
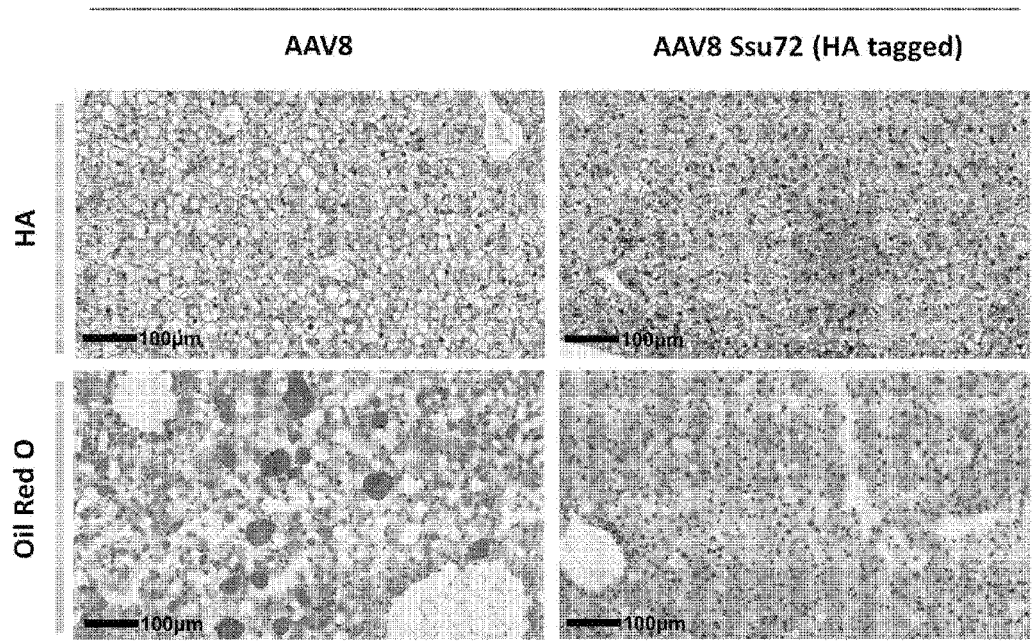

FIG. 5A shows a series of photographs representing immunohistochemical analysis of expression level of Ssu72 peptide in the liver tissue section from the groups administrated with AAV (control) and AAV8 Ssu72 viruses, respectively (top) and a series of photographs representing an analysis of lipid deposition in the liver of the experimental animals through Oil Red O staining (bottom), representing the results of morphological and histological analysis in the non-alcoholic steatohepatitis lesions in the experimental animals after the injection of the AAV8 Ssu72 viruses into the experimental animal after applying non-alcoholic steatohepatitis-inducing diet (MCD):

Expression of HA-tagged Ssu72: anti-HA antibodies; and

Staining of fat: Oil Red O.

Figure 5B:
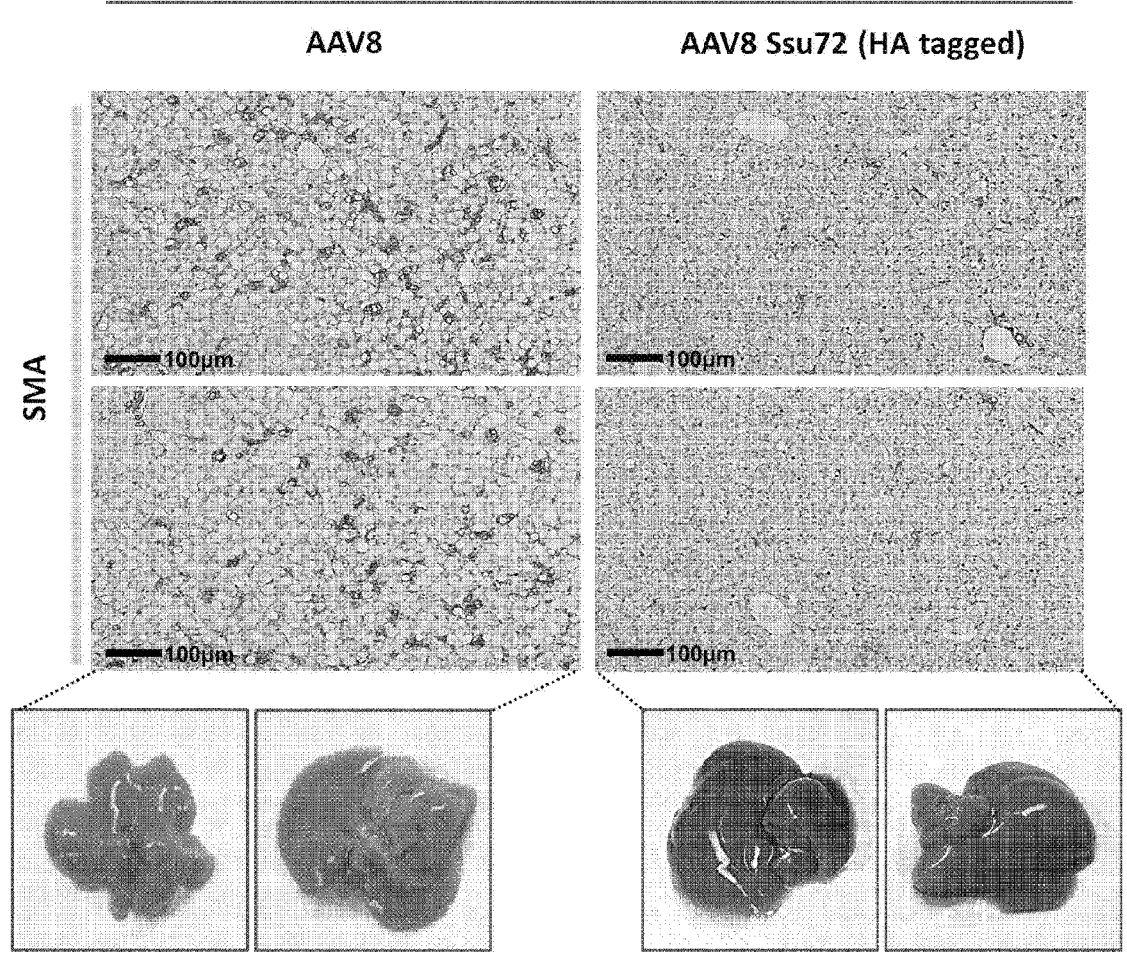

FIG. 5B shows a series of photographs showing overall appearances of the liver excised from the experimental animals as shown in FIG. 5a (top) and a photograph representing the result of immunohistochemical analysis of the liver tissue sections using anti-SMA antibodies.

Figure 6:
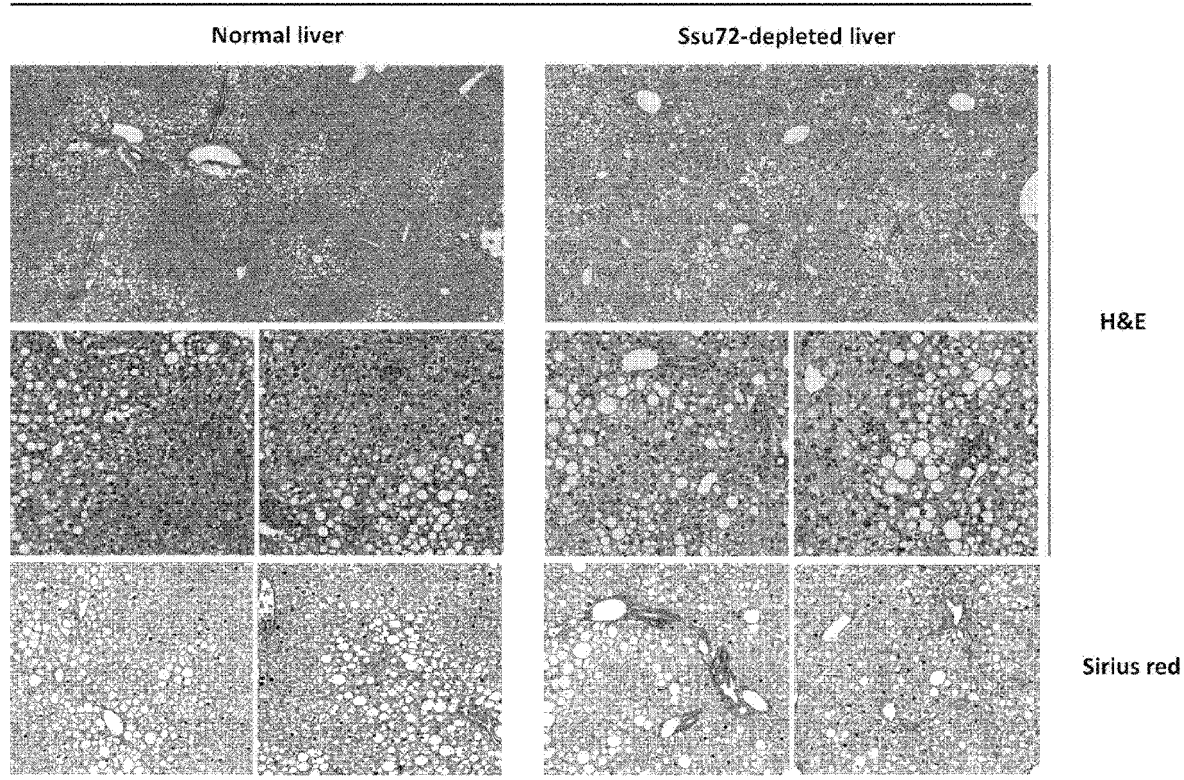

FIG. 6 is a series of microscopic photographs of liver tissue sections after H&E staining and Sirius Red staining after excising livers from the experimental animals at 3 months after inducing another non-alcoholic steatohepatitis-inducing diet including Western diet supplemented with fructose to normal mice (control group) and transgenic mice (experimental group) whose liver-specific expression of Ssu72 is suppressed, representing an analysis result performed to verify the role of the Ssu72 gene in the transgenic mice through the non-alcoholic steatohepatitis-inducing diet.

Figure 7A:
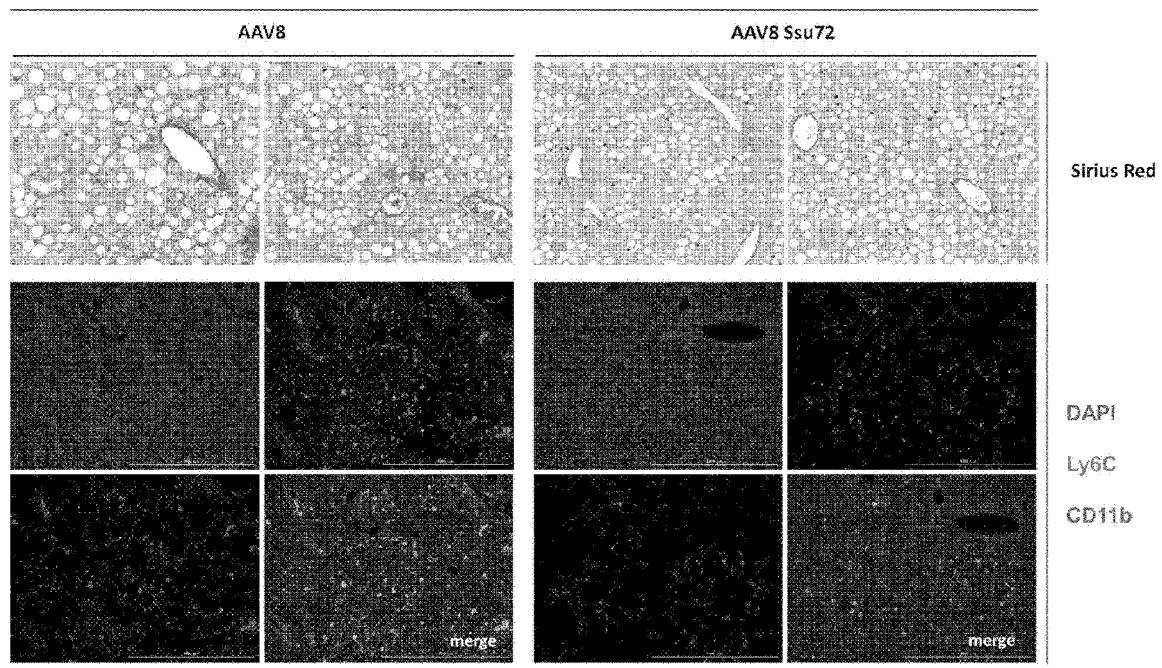

FIG. 7A is a series of microscopic photographs representing the results of immunohistochemical analysis using anti-Ly6c and anti-CD11b antibodies and Sirius red staining for liver tissue sections excised from experimental animals sacrificed after applying choline-deficient and high fat diet (CD+HFD), which is one of experimental models.

Figure 7B:
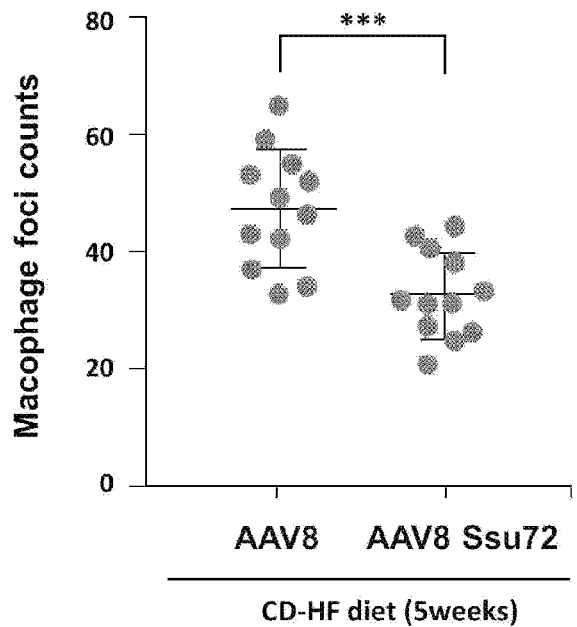

FIG. 7B is a graph representing the results of measuring and analyzing the number of foci in which at least five macrophages are gathered to quantify the amount of inflammatory macrophages measured in FIG. 7A, representing the effectiveness of alleviating and treating inflammatory syndromes of non-alcoholic steatohepatitis of the AAV8 Ssu72 viruses according to an embodiment of the present invention.

Figure 7C:
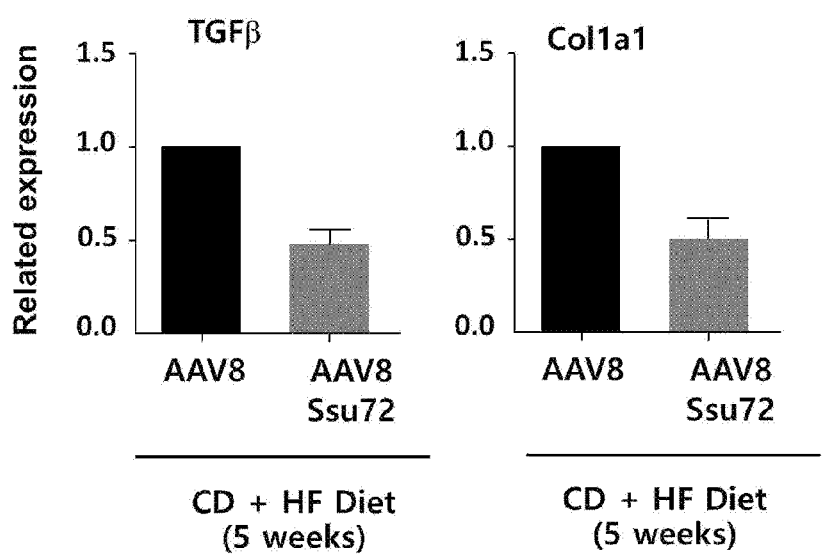

FIG. 7C is a graph representing the results of analyzing the expression of the TGF-β and Col1a1 genes, indicators of fibrosis in mice with five weeks of CD+HFD administrated with AAV8 Ssu72.

Figure 8A:
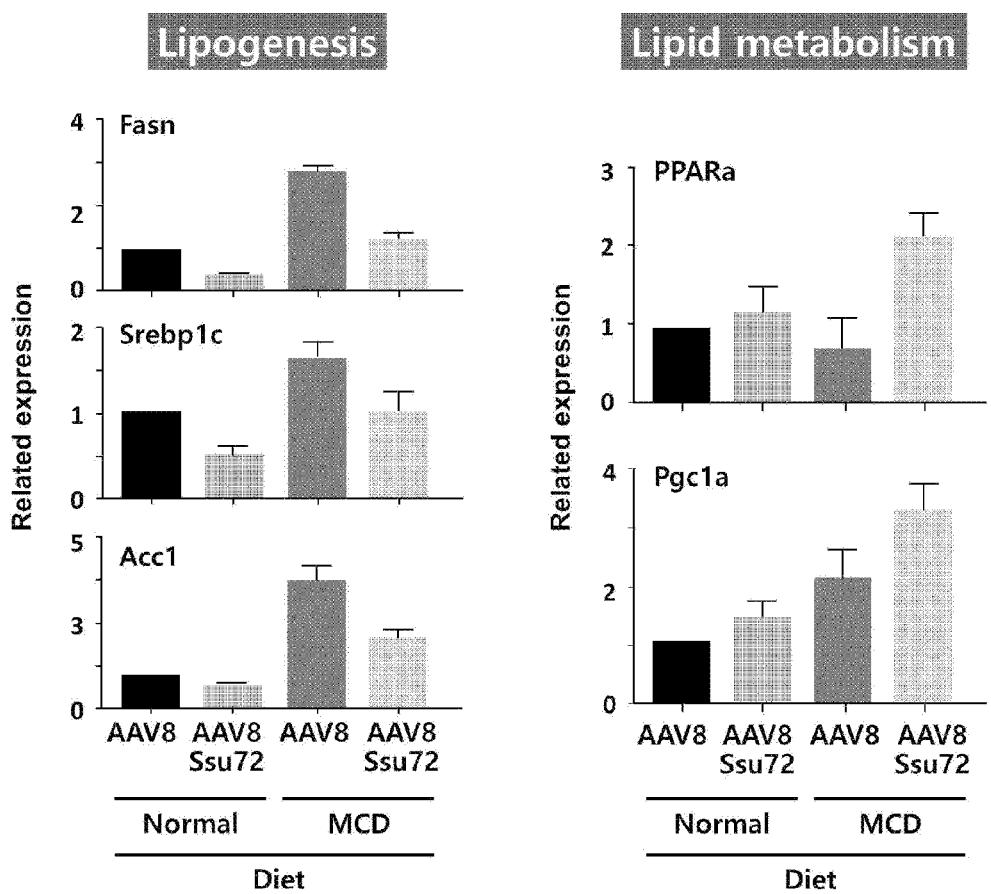

FIG. 8A is a graph representing the results of real-time qRT-PCR analysis using liver tissue after administration of the AAV8 Ssu72 viruses to experimental mice. After administering the AAV8 Ssu72 viruses according to an embodiment of the present invention to mice after applying normal diet and non-alcoholic steatohepatitis-induced diet (MCD diet), respectively, expression levels of Fasn, Srebp1c, and Acc1, which are lipogenesis-related genes, PPARα and PCG1α, which are lipid metabolism-related genes were analyzed.

Figure 8B:
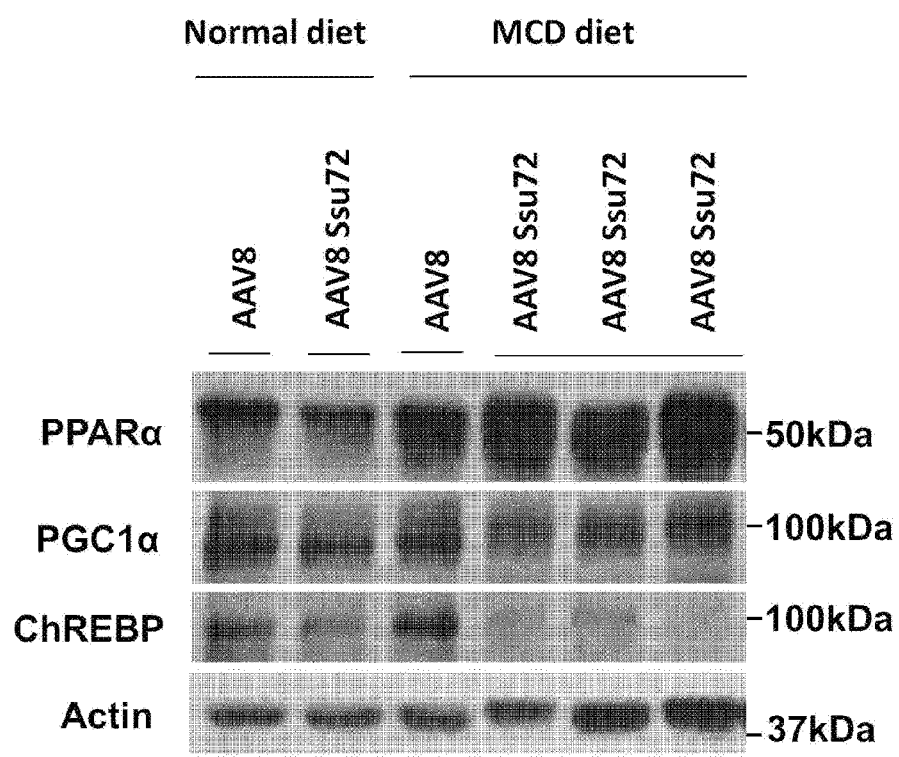

FIG. 8B is a series of photographs representing the results of western blot analysis of changes in the expression level of ChREBP which is a protein related to De novo lipogenesis in the mice liver and PPARα and PGC1α which are proteins related to lipid metabolism when normal diet and non-alcoholic steatohepatitis-inducing diet (MCD diet) were performed after administrating AAV8 Su72 viruses to mice, representing the results of western blotting analysis of changes in the expression of lipid metabolism-related proteins after administration of the AAV8 Ssu72 viruses according to an embodiment of the present invention to experimental mice.

Figure 8C:
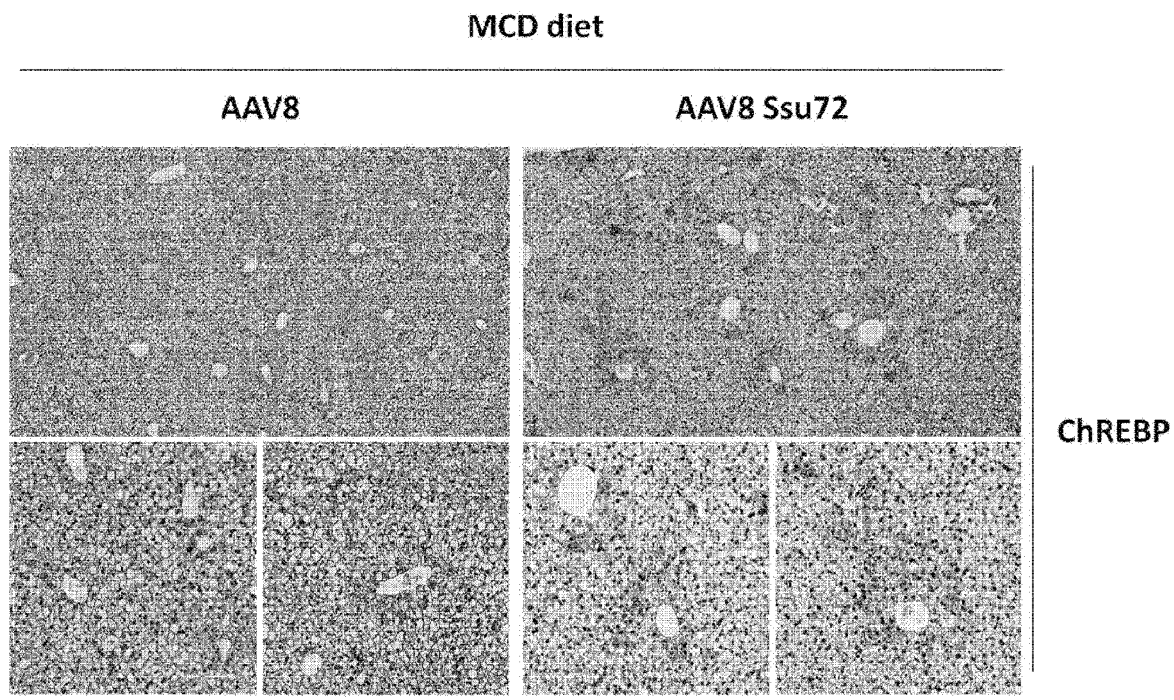

FIG. 8C is a series of microscopic photographs representing the results of immunohistochemical analysis using anti-ChREBP antibodies for measuring the expression level of ChREBP, which is a protein related to de novo lipogenesis in the liver from the liver tissues excised from experimental animals when normal diet and non-alcoholic steatohepatitis-inducing diet were performed, respectively after administrating the AAV8 Ssu72 viruses according to an embodiment of the present invention to experimental mice in order to evaluate the effectiveness of preventing and treating steatohepatitis of the AAV8 Ssu72 viruses.

Figure 9A:
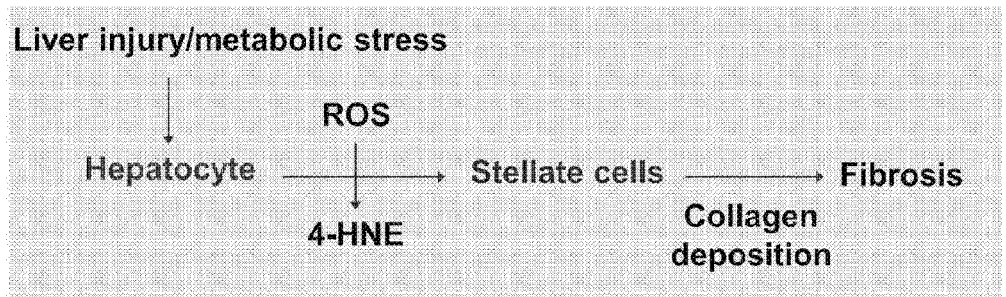
Figure 9A:
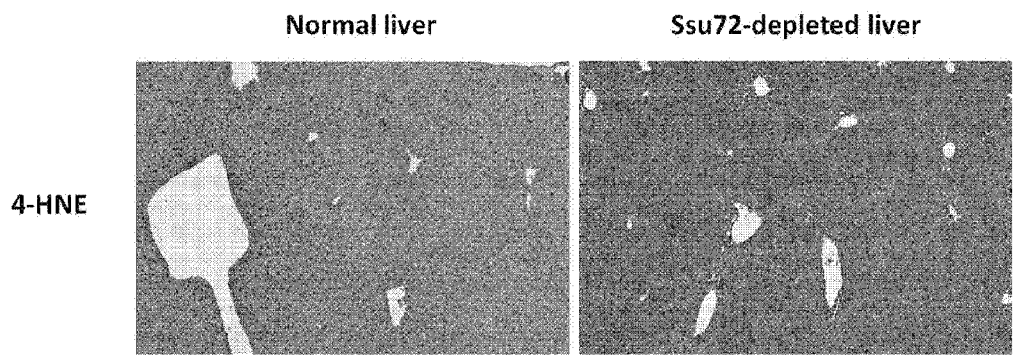

FIG. 9A is a series of immunostaining photographs representing the results of observation of the formation of ROS and an abnormal metabolite (4-HNE) in non-alcoholic steatohepatitis liver tissues, after injecting the AAV8 Ssu72 viruses into mice.

Figure 9B:
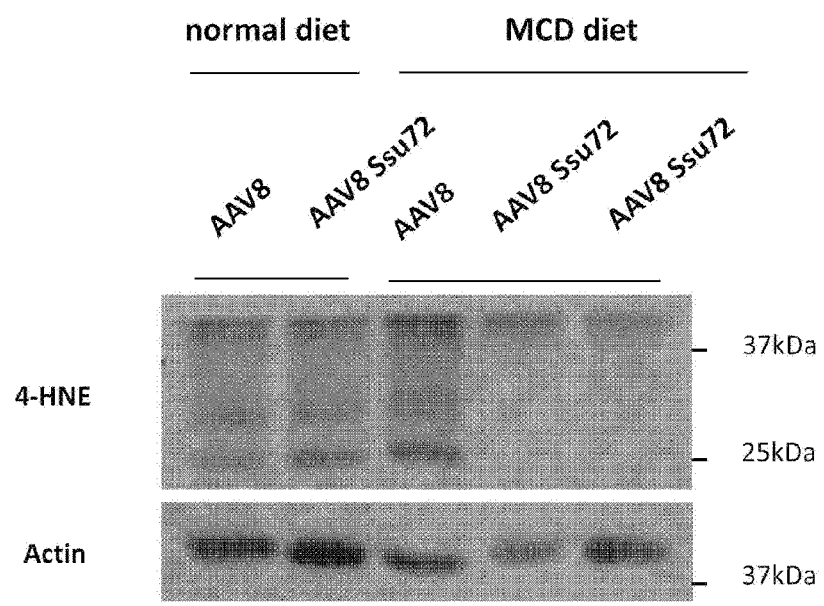

FIG. 9B is a series of photographs shows the results of western blot analysis in order to determine the degree of induction of abnormal metabolites produced through liver damage caused by various metabolic stresses, representing the results of observation of the formation of ROS and an abnormal metabolites (4-HNE) in non-alcoholic steatohepatitic liver tissues after injecting the AAV8 Ssu72 viruses into mice.

FIG. 10A is a graph showing the results of analyzing the expression levels of fibrosis-related genes, TGF-β, Col1a1, Co13a1, and MMP12 with qRT-PCR, confirming the inhibition of liver fibrosis mechanism in non-alcoholic steatohepatitic liver tissues after injecting the AAV8 Ssu72 viruses into mice.

Figure 10B:
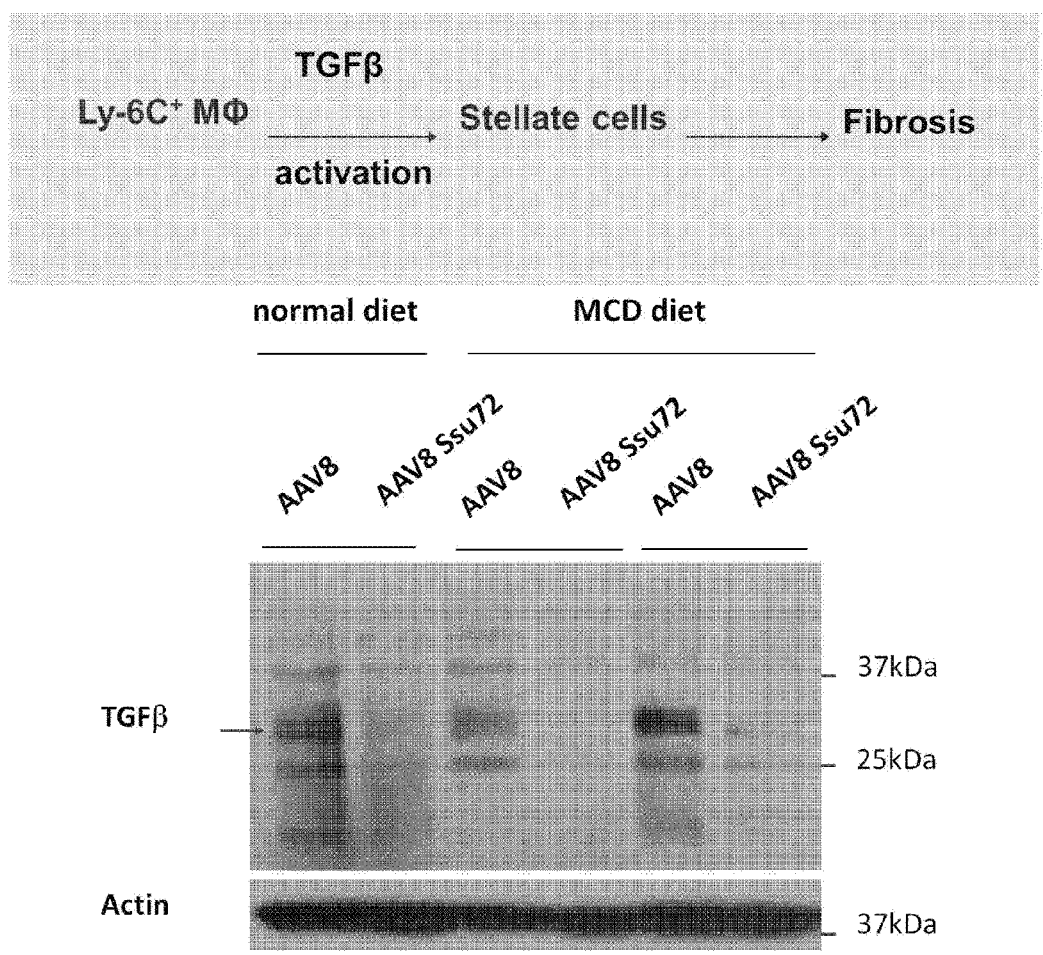

FIG. 10B is a photograph showing the results of analysis of the expression level of fibrosis-related TGF-β in liver fibrotic tissues after injecting AAV8 Ssu72 viruses into mice.

Figure 11A:
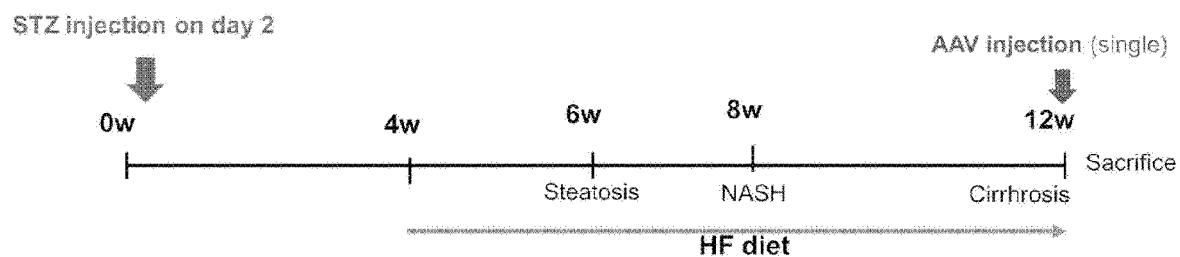

FIG. 11A is a schematic diagram representing an experimental schedule of model animal experiment in order to evaluate the therapeutic effect of AAV8 Ssu72 according to an embodiment of the present invention on non-alcoholic steatohepatitis and liver fibrosis after inducing non-alcoholic steatohepatitis using the STAM model, and then AAV8 Ssu72 virus is administered to model animals.

Figure 11B:
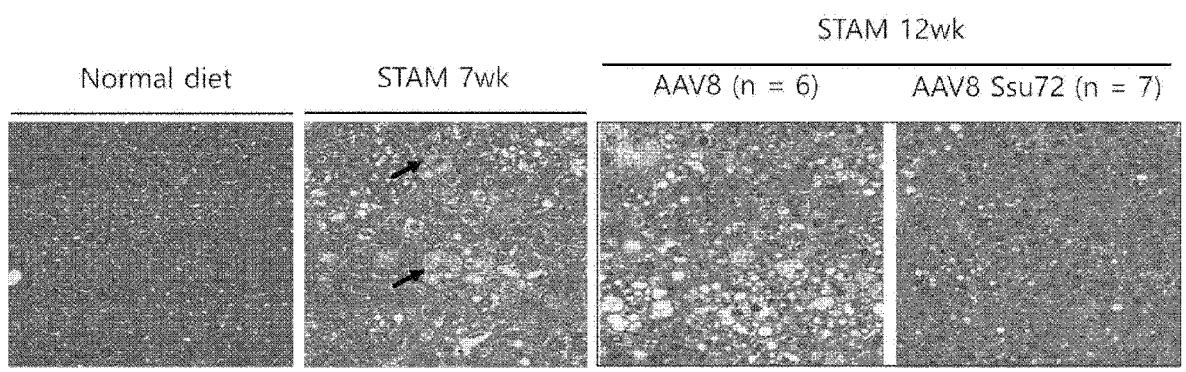

FIG. 11B is a series of microscopic photographs representing H&E staining of liver tissues excised from groups administrated with control AAV8 and AAV8 Ssu72 viruses according to an embodiment of the present invention, respectively after performing experiments as scheduled in FIG. 11A, representing the therapeutic effect of AAV8 Ssu72 viruses according to an embodiment of the present invention on NASH after inducing NASH using STAM model.

Figure 11C:
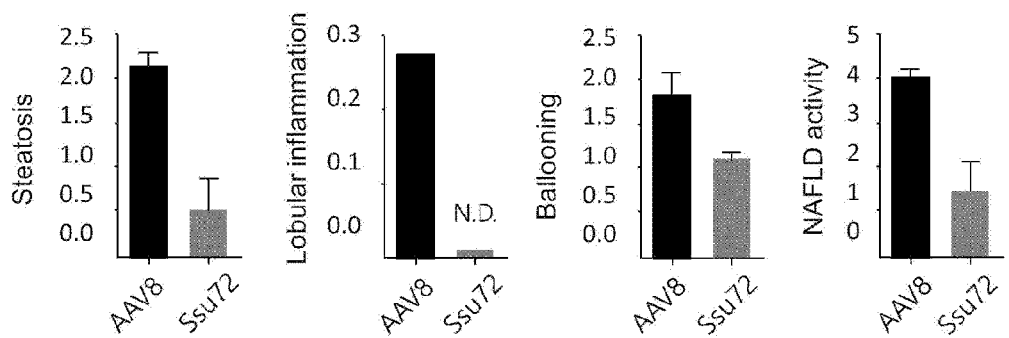

FIG. 11C is a graph showing the results of analyzing the results of various measurement indexes in order to evaluate the therapeutic effects of AAV8 Ssu72 viruses according to an embodiment of the present invention on non-alcoholic steatohepatitis and hepatic fibrosis after inducing non-alcoholic steatohepatitis using the STAM model. In the group administered the control AAV8 viruses and the group administered the AAV8 Ssu72 viruses, steatosis, global inflammation, ballooning of hepatocytes, non-alcoholic steatohepatitis score (NAFLD activity, NAS), liver damage index (AST, ALT), and the degree of liver fibrosis (Sirius Red-positive area) were determined. In the graph, the Y-axis value represents NAS score, which means a NASH CRN scoring system widely used as a semi-quantitative verified scoring system. The NASH CRN scoring system includes NAFLD activity scores (NAS), which include a combination of ballooning in the range of 0-8 points, lobular inflammation, and steatosis in the range of 0-4 points (Arka De et al., *J. Clin. Exp. Hepatol.* 10(3): 255-262. 2020).

Figure 12A:

FIG. 12A is a schematic diagram representing an animal experiment in order to evaluate the therapeutic effect of AAV8 Ssu72 viruses according to an embodiment of the present invention on non-alcoholic steatohepatitis and hepatic fibrosis. The present inventors evaluated the therapeutic effect of AAV8 Ssu72 viruses according to an embodiment after inducing non-alcoholic steatohepatitis when administrating the AAV8 Ssu72 viruses into experimental mice who were applied with normal diet and non-alcoholic steatohepatitis-inducing diet using the CDA+HFD (choline-deficient, L-amino acid-deficient, high-fat diet) and HFD (high-fat diet), respectively.

Figure 12B:
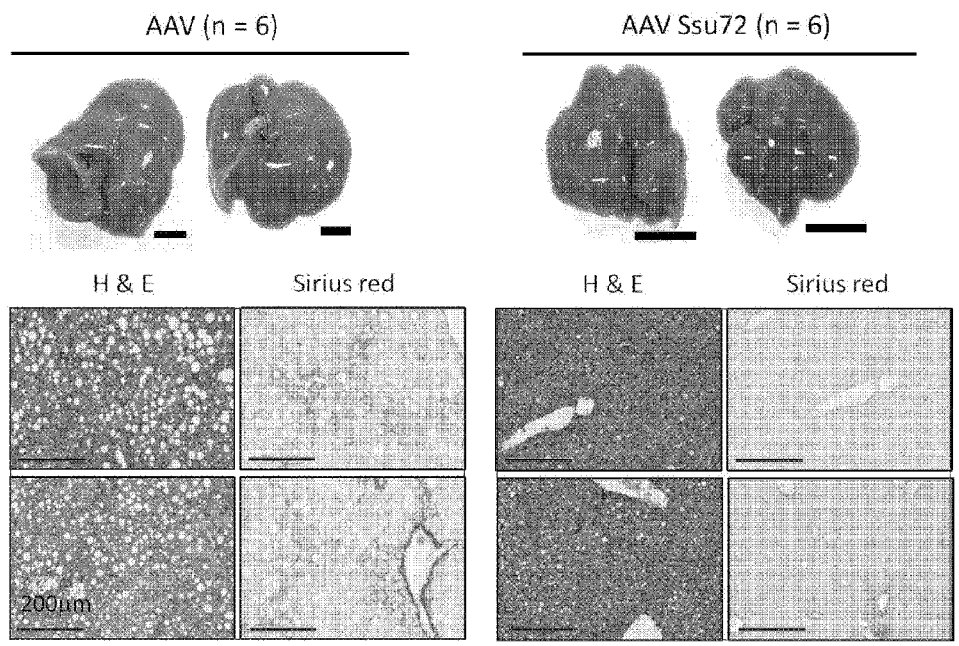

FIG. 12B is a series of photographs representing the results of the observation of overall appearances of livers (top), H&E staining of liver tissue sections (left bottom) and Sirius red staining of liver tissue sections (right bottom) after performing animal experiment as scheduled in FIG. 12A, representing the results of analyzing the therapeutic effects of AAV8 Ssu72 viruses according to an embodiment of the present invention on non-alcoholic steatohepatitis and hepatic fibrosis after inducing non-alcoholic steatohepatitis using the CDAHFD model.

Figure 12C:
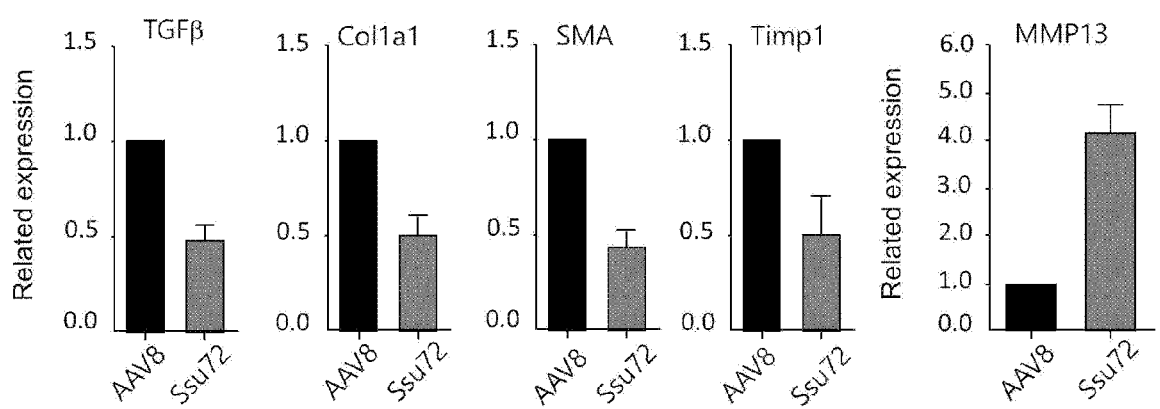

FIG. 12C is a graph representing the results of confirming expression of TGF-β, Col1a1, SMA, and Timp1, indicators of progress of liver fibrosis, and MMP13, which is an indicator of improvement of liver fibrosis, using qRT-PCT, when administrating control (AAV8) viruses and AAV8 Ssu72 viruses to experimental mice, respectively, indicating the therapeutic effect of the AAV8 Ssu72 viruses according to an embodiment of the present invention on non-alcoholic steatohepatitis and hepatic fibrosis after inducing non-alcoholic steatohepatitis using CDAHFD model.

DETAILED DESCRIPTION

Definition of Terms

As used herein, the term "non-alcoholic steatohepatitis (NASH)" refers to a disease showing pathological features such as ballooning degeneration, apoptosis, and inflammatory infiltration, unlike simple fatty diseases, and in some cases, may show pathological features of fibrosis such as collagen accumulation. It is well known that non-alcoholic steatohepatitis shows faster histological progression whereas simple fatty liver shows slow histological progression and can progress to cirrhosis, and about 5-10% of those who have been diagnosed as fatty liver are found to be steatohepatitis.

As used herein, the term "Ssu72 peptide" or "Ssu72 peptide" is known as a dephosphorylation enzyme that catalyzes dephosphorylation of the C-terminal domain of RNA polymerase II in a yeast model, but it's in vivo function is not well known in higher animals. The genes and proteins are all conserved from yeast to chimpanzees, dogs, pigs, mice, rats, and the like, and specific nucleotide sequences and protein information are known from NCBI (NCBI Reference Sequence: NM_026899.3, NM_200728.1, etc.).

DETAILED DESCRIPTION OF THE INVENTION

In an aspect of the present invention, there is provided a method for treating a patient suffering from a liver disease selected from the group consisting of non-alcoholic fatty liver, non-alcoholic steatohepatitis and hepatic fibrosis comprising administrating at least one selected from the group consisting of:

an Ssu72 peptide, a polynucleotide encoding the Ssu72 peptide, and an expression vector comprising the polynucleotide.

In the method, the Ssu72 peptide may have the amino acid sequence represented by SEQ ID NO: 1.

In the method, the Ssu72 peptide may be encoded by a polynucleotide having the nucleotide sequence represented by SEQ ID NO: 2.

In the method, the polynucleotide may be DNA or RNA.

In the method, the expression vector may be a viral vector or a non-viral vector.

In the method, the viral vector may be an adeno-associated virus (AAV) vector, an adenovirus vector, an alphavirus vector, a herpes simplex virus vector, a vaccinia virus vector, a Sendai virus vector, a flavivirus vector, a radovirus vector, a retroviral vector, a herpesvirus vector, a poxvirus vector or a lentiviral vector. In a preferred embodiment, the viral vector may be an adeno-associated virus (AAV) vector.

In the method, the non-viral vector may be a DNA vector, a nanoparticle, a cationic polymer, an exosome, an extracellular vesicle or a liposome.

In the method, the DNA vector may be a plasmid vector, a cosmid vector, a phagemid vector, or an artificial human chromosome.

In the method, the vector may comprise a gene construct in which the polynucleotide encoding the Ssu72 peptide is operably linked to a promoter.

In the method, the promoter may be a constitutive promoter, an inducible promoter, or a liver-specific promoter. The constitutive promoter may be a CMV-HSV thymidine kinase promoter, a CMV promoter, an SV40 promoter, an RSV (Rous sarcoma virus) promoter, a human kidney urea 1α-promoter. The inducible promoter may be a glucocorticoid-inducible MMTV (Moloney mouse tumor virus) promoter, a metallothionein-inducible promoter, a tetracycline-inducible promoter. The liver-specific promoter may be a thyroxin-binding globulin (TBG) promoter, a PB GD promoter, an α-1 anti-trypsin promoter (EhAlbAAT), an Hepatic Control Region (HCR)-ApoCII hybrid promoter, an HCR-hAAT hybrid promoter, an apolipoprotein E (ApoE) promoter, a phosphoglycerate kinase [PGK] promoter, or a hybrid liver-specific promoter (HLP). In a preferred embodiment, the liver-specific promoter may be a thyroxin-binding globulin (TBG) promoter. The TBD promoter may comprises the nucleotide sequence of SEQ ID NO: 3.

In the method, wherein the patient may show lower expression or activity of Ssu72 peptide in the liver than a normal subject. Otherwise, the Ssu72 peptide may be expressed as an inactive form in the liver of the patient.

In an aspect of the present invention, there is provided a method for treating a liver disease selected from a group consisting of non-alcoholic fatty liver, non-alcoholic steatohepatitis and hepatic fibrosis in a subject comprising:

measuring the expression level or activity of an Ssu72 peptide in a sample obtained from the subject; and administrating at least on selected from the group consisting of i) to iii) to the subject when the expression level of the Ssu72 peptide in the subject is lower than that of normal subjects or the Ssu72 is expressed in an inactive form;

i) an Ssu72 peptide having an amino acid sequence represented by SEQ ID NO: 1, ii) a polynucleotide encoding the Ssu72 peptide, and iii) an expression vector containing the polynucleotide.

In the method, the sample may be a liver tissue biopsy or a body fluid, and the body fluid may be saliva, blood, serum, plasma, urine, tears or sweat. In addition, the polynucleotide may be DNA or RNA.

In the method, the Ssu72 peptide may be encoded by a polynucleotide having the nucleotide sequence represented by SEQ ID NO: 2.

In the method, the polynucleotide may be DNA or RNA.

In the method, the expression vector may be a viral vector or a non-viral vector.

In the method, the viral vector may be an adeno-associated virus (AAV) vector, an adenovirus vector, an alphavirus vector, a herpes simplex virus vector, a vaccinia virus vector, a Sendai virus vector, a flavivirus vector, a radovirus vector, a retroviral vector, a herpesvirus vector, a poxvirus vector or a lentiviral vector. In a preferred embodiment, the viral vector may be an adeno-associated virus (AAV) vector.

In the method, the non-viral vector may be a DNA vector, a nanoparticle, a cationic polymer, an exosome, an extracellular vesicle or a liposome.

In the method, the DNA vector may be a plasmid vector, a cosmid vector, a phagemid vector, or an artificial human chromosome.

In the method, the vector may comprise a gene construct in which the polynucleotide encoding the Ssu72 peptide is operably linked to a promoter.

In the method, the promoter may be a constitutive promoter, an inducible promoter, or a liver-specific promoter. The constitutive promoter may be a CMV-HSV thymidine kinase promoter, a CMV promoter, an SV40 promoter, an RSV (Rous sarcoma virus) promoter, a human kidney urea 1α-promoter. The inducible promoter may be a glucocorticoid-inducible MMTV (Moloney mouse tumor virus) promoter, a metallothionein-inducible promoter, a tetracycline-inducible promoter. The liver-specific promoter may be a thyroxin-binding globulin (TBG) promoter, a PBGD promoter, an α-1 anti-trypsin promoter (EhAlbAAT), an Hepatic Control Region (HCR)-ApoCII hybrid promoter, an HCR-hAAT hybrid promoter, an apolipoprotein E (ApoE) promoter, a phosphoglycerate kinase [PGK] promoter, or a hybrid liver-specific promoter (HLP). In a preferred embodiment, the liver-specific promoter may be a thyroxin-binding globulin (TBG) promoter. The TBD promoter may comprises the nucleotide sequence of SEQ ID NO: 3.

In another aspect of the present invention, provided are a method for preventing a liver disease selected from the group consisting of non-alcoholic fatty liver, non-alcoholic steatohepatitis and hepatic fibrosis in a subject, comprising administering at least one selected from the group consisting of i) to iii) to the subject:
  i) an Ssu72 peptide having an amino acid sequence represented by SEQ ID NO: 1,
  ii) a polynucleotide encoding the Ssu72 peptide, and
  iii) an expression vector containing the polynucleotide.

In the method, the Ssu72 peptide may be encoded by a polynucleotide having the nucleotide sequence represented by SEQ ID NO: 2.

In the method, the polynucleotide may be DNA or RNA.

In the method, the expression vector may be a viral vector or a non-viral vector.

In the method, the viral vector may be an adeno-associated virus (AAV) vector, an adenovirus vector, an alphavirus vector, a herpes simplex virus vector, a vaccinia virus vector, a Sendai virus vector, a flavivirus vector, a radovirus vector, a retroviral vector, a herpesvirus vector, a poxvirus vector or a lentiviral vector. In a preferred embodiment, the viral vector may be an adeno-associated virus (AAV) vector.

In the method, the non-viral vector may be a DNA vector, a nanoparticle, a cationic polymer, an exosome, an extracellular vesicle or a liposome.

In the method, the DNA vector may be a plasmid vector, a cosmid vector, a phagemid vector, or an artificial human chromosome.

In the method, the vector may comprise a gene construct in which the polynucleotide encoding the Ssu72 peptide is operably linked to a promoter.

In the method, the promoter may be a constitutive promoter, an inducible promoter, or a liver-specific promoter. The constitutive promoter may be a CMV-HSV thymidine kinase promoter, a CMV promoter, an SV40 promoter, an RSV (Rous sarcoma virus) promoter, a human kidney urea 1α-promoter. The inducible promoter may be a glucocorticoid-inducible MMTV (Moloney mouse tumor virus) promoter, a metallothionein-inducible promoter, a tetracycline-inducible promoter. The liver-specific promoter may be a thyroxin-binding globulin (TBG) promoter, a PBGD promoter, an α-1 anti-trypsin promoter (EhAlbAAT), an Hepatic Control Region (HCR)-ApoCII hybrid promoter, an HCR-hAAT hybrid promoter, an apolipoprotein E (ApoE) promoter, a phosphoglycerate kinase [PGK] promoter, or a hybrid liver-specific promoter (HLP). In a preferred embodiment, the liver-specific promoter may be a thyroxin-binding globulin (TBG) promoter. The TBD promoter may comprises the nucleotide sequence of SEQ ID NO: 3.

In the method, the subject may show lower expression level or activity of the Ssu72 peptide in the liver than a normal subject or the Ssu72 peptide is expressed as an inactive form in the liver.

In another aspect of the present invention, there is provided a method for diagnosing non-alcoholic steatohepatitis in a patient suffering from a liver disease comprising:
  measuring the expression level or activity of an Ssu72 peptide in a sample obtained from the patient; and
  diagnosing the patient as one having non-alcoholic steatohepatitis when the expression level of the Ssu72 peptide in the patient is lower than that of normal subjects or the Ssu72 peptide is expressed in an inactive form in the patient.

In the method, the sample may be a liver tissue biopsy or a body fluid, and the body fluid may be saliva, blood, serum, plasma, urine, tears or sweat.

In the method, the expression level or activity of an Ssu72 peptide may be measured by a process known in the art. The process may include an RT-PCR, an ELISA, a RIA (radio-immunoassay), a Western blot assay, a phosphatase activity assay. The phosphatase activity assay may be performed by using a C-terminal domain of RNA polymerase II as a substrate.

In the present invention, the Ssu72 peptide may be composed of the amino acid sequence represented by SEQ ID NO: 1. Alternatively, a peptide having at least 70%, preferably at least 80%, more preferably at least 90% homology with the amino acid sequence represented by SEQ ID NO: 1, most preferably a peptide having at least 95%, 96%, 97%, 98% or 99% sequence homology with the amino acid sequence represented by SEQ ID NO: 1 may be used if it has biological activity of Ssu72.

In an exemplary embodiment of the present invention, a gene construct was prepared so that the HA tag was included in the Ssu72 peptide consisting of the amino acid sequence represented by SEQ ID NO: 1. The reason to add the HA tag is to distinguish a recombinant Ssu72 peptide expressed by transduction from inherent Ssu72 peptide when performing analyses such as Western blotting analysis, since the Ssu72 peptide expressed by gene transduction is indistinguishable from the endogenous Ssu72 peptide in the body. Therefore, the actual gene construct for therapeutic or prophylactic use may include a tag for identification such as an HA tag, or it may be removed to minimize immunogenicity.

In the present invention, the nucleotide encoding the Ssu72 peptide may encoded by a polynucleotide having a nucleotide sequence represented by SEQ ID NO: 2.

The expression vector of the present invention may be any recombinant vector that is generally manufactured, may include both non-viral vectors and viral vectors, and preferably may be recombinant viral vectors, but is not limited thereto.

The expression vector may further include a polynucleotide encoding a secretion signal sequence, and the secretion signal sequence induces the extracellular secretion of the recombinant protein expressed in the cell, and may be a tissue plasminogen activator (tPA) signal sequence, a herpes simplex virus glycoprotein Ds (HSV gDs) signal sequence, or a growth hormone signal sequence.

In addition, the polynucleotide encoding the Ssu72 peptide according to an embodiment of the present invention may be included in an expression vector in the form of a gene construct operably linked to a regulatory sequence for constitutive expression or spatio-temporal expression in a subject.

As used herein, the term "operably linked to" means that a target nucleic acid sequence (for example, in vitro transcription/translation system or in a host cell) is linked to the regulatory sequence in such a way that the target nucleic acid sequence can be expressed.

As used herein, the term "regulatory sequence" is meant to include a promoter, an enhancer, and other regulatory elements (for example, polyadenylation signal). Examples of the regulatory sequence include a sequence which directs such that a target nucleic acid is constantly expressed in many host cells, a sequence (for example, a tissue-specific regulatory sequence) which directs such that a target nucleic acid is expressed only in a specific tissue cell, and a sequence (for example, an inducible regulatory sequence) which directs such that expression is induced by a specific signal. Those skilled in the art could understand that the design of an expression vector may vary depending on factors such as the selection of a host cell to be transformed and the desired level of protein expression. Regulatory sequences which enable expression in the eukaryotic cell and the prokaryotic cell are well known to those skilled in the art. As described above, these regulatory sequences generally include regulatory sequences responsible for transcription initiation, and optionally, a poly-A signal responsible for transcription termination and stabilization of a transcript. Additional regulatory sequences may include a translation enhancing factor and/or a naturally-combined or heterologous promoter region, in addition to the transcription regulatory factor. For example, possible regulatory sequences which enable expression in a mammalian host cell include a CMV-HSV thymidine kinase promoter, SV40, an RSV (Rous sarcoma virus)-promoter, a human kidney urea 1α-promoter, a glucocorticoid-inducing MMTV (Moloney mouse tumor virus)-promoter, a metallothionein- or tetracycline-inducible promoter, or an amplifying agent such as a CMV promoter and an SV40 promoter.

In another aspect of the present invention, there is provided a pharmaceutical composition for treating liver disease selected from the group consisting of non-alcoholic fatty liver, non-alcoholic steatohepatitis, and liver cirrhosis comprising at least one selected from the group consisting of:
  i) an Ssu72 peptide having an amino acid sequence represented by SEQ ID NO: 1,
  ii) a polynucleotide encoding the Ssu72 peptide, and
  iii) an expression vector containing the polynucleotide.

In an aspect of the present invention, there is provided a pharmaceutical composition for preventing liver disease selected from the group consisting of non-alcoholic fatty liver, non-alcoholic steatohepatitis, and liver cirrhosis comprising at least one selected from the group consisting of:
  i) an Ssu72 peptide having an amino acid sequence represented by SEQ ID NO: 1,
  ii) a polynucleotide encoding the Ssu72 peptide, and
  iii) an expression vector containing the polynucleotide.

In another aspect of the present invention, provided is a nutraceutical composition capable of helping liver health, comprising at least on selected from the group consisting of
  i) an Ssu72 peptide having an amino acid sequence represented by SEQ ID NO: 1,
  ii) a polynucleotide encoding the Ssu72 peptide, and
  iii) an expression vector containing the polynucleotide.

In the pharmaceutical composition, the expression vector may be a viral vector or a non-viral vector. The viral vector may be an adeno-associated virus (AAV) vector, an adenovirus vector, an alphavirus vector, a herpes simplex virus vector, a vaccinia virus vector, a Sendai virus vector, a flavivirus vector, a radovirus vector, a retroviral vector, a herpesvirus vector, a poxvirus vector or a lentiviral vector. The non-viral vector may be a DNA vector, a nanoparticle, a cationic polymer, an exosome, an extracellular vesicle or a liposome. The DNA vector may be a plasmid vector, a cosmid vector, a phagemid vector, or an artificial human chromosome.

It is considered that for expression in the liver, a liver specific promoter, such as PBGD promoter, α-1 anti-trypsin promoter (EhAlbAAT), a thyroxin-binding globulin (TB G) promoter, an Hepatic Control Region (HCR)-ApoCII hybrid promoter, an HCR-hAAT hybrid promoter, an apolipoprotein E (ApoE) promoter, phosphoglycerate kinase [PGK] promoter, hybrid liver-specific promoter [HLP], or a liver-specific promoter disclosed in prior arts (WO2001098482A; WO2020104782A) can be used.

The abovementioned promoters are known in the art, and are described in the literature (Charron, *J. Biol. Chem.* 270: 25739-25745, 1995). For the expression in the prokaryotic cell, a number of promoters, including a lac-promoter, a tac-promoter, or a trp promoter, have been disclosed. In addition to the factors capable of initiating transcription, the regulatory sequences may include a transcription termination signal, such as an SV40-poly-A site and a TK-poly-A site, on the downstream of the polynucleotide according to one exemplary embodiment of the present invention. In the present specification, suitable expression vectors are known in the art, and examples thereof include Okayama-Berg cDNA expression vector pcDV1 (Parmacia), pRc/CMV, pcDNA1, pcDNA3 (Invitrogen), pSPORT1 (GIBCO BRL), pGX-27 (Korean Patent No. 1442254), pX (Pagano et al., *Science* 255: 1144-1147, 1992), a yeast two-hybrid vector such as pEG202 and dpJG4-5 (Gyuris et al., *Cell* 75: 791-803, 1995), and a prokaryotic expression vector such as lambda gt11 and pGEX (Amersham Pharmacia). The vector may further include a polynucleotide encoding a secretion signal, in addition to the nucleic acid molecules of the present invention. The secretion signals are well known to those skilled in the art. Moreover, depending on the used expression system, a leader sequence which can lead the protein according to one exemplary embodiment of the present invention to a cellular compartment is combined with a coding sequence of the polynucleotide according to one exemplary embodiment of the present invention, and is preferably a leader sequence capable of directly secreting a decoded protein or the protein thereof into a pericytoplasmic or extracellular medium.

In addition, the gene construct may be provided in the form of an expression vector such as a plasmid vector for convenience of manufacture and operation.

In addition, the vector of the present invention can be prepared, for example, by a standard recombinant DNA technique, and examples of the standard recombinant DNA technique include ligation of a smooth terminus and an adhesion terminus, a restriction enzyme treatment to provide a proper terminus, removal of a phosphate group by an alkaline phosphatase treatment to prevent inappropriate binding, and enzymatic linkage by T4 DNA ligase. The vector of the present invention can be prepared by recombining DNA encoding a signal peptide obtained by chemical synthesis or a genetic recombination technique, and a polynucleotide encoding the Ssu72 peptide according to one exemplary embodiment of the present invention, with a vector containing an appropriate regulatory sequence. The vector containing a regulatory sequence can be commercially purchased or prepared.

If the composition according to this invention is in the form of a nutraceutical composition, it may be manufactured as a food with high medical and medical effects to efficiently exhibit bio-control functions, and in some cases, it may be alternatively named as "functional food", "heath food" or "dietary supplement" and may be formulated in a form of capsule, powder, tablet, granule, liquid, or pillet.

The nutraceutical composition of the present invention may include additional components that are commonly used in food compositions to improve odor, taste, and sight. For example, vitamins A, C, D, E, B1, B2, B6, B12, niacin, biotin, polate, pantotenic acid, and the like may be included. In addition, minerals such as zinc (Zn), iron (Fe), calcium (Ca), chromium (Cr), magnesium (Mg), manganese (Mn), and copper (Cu) may be included. In addition, amino acids such as lysine, tryptophan, cysteine, and valin may be included. In addition, preservatives (potassium sorbate, sodium benzoate, salicylic acid, sodium dihydrochlorite, etc.), disinfectants (bleach power, higher bleach powder, and sodium hypochlorite, etc.), antioxidants (butylhydroxy toluene (BHT), colorants (tar pigment), color developer (sodium nitrite, sodium acetate, etc.), beach (sodium sulfite), seasonings (sodium glutamate), sweetner (dulcine, cyclmate, sodiu, saccharin, etc.), expanders (plaster, D-potassium hydrogen trartrate, etc.), emulsifying agent, fortifying agent, thickener, film forming agent, gum base, defoaming agent, solvent and conditioner, etc. The additives may be selected according to the type of nutraceutical composition and used in an appropriate amount.

When the nutraceutical composition of the present invention is used as a food additive, the same may be added as it is or used in combination with other food or food components, and may be appropriately used according to a conventional method.

In the nutraceutical composition of the present invention, the amount of Ssu72 peptide or a polynucleotide encoding the same is not particularly limited, and may be variously changed according to the state to be administered, the type of specific pathogenesis, and the like. If necessary, it may also be included in the total content of the food.

In another aspect of the present invention, there is provided use of i) Ssu72 peptide having an amino acid sequence represented by SEQ ID NO: 1, ii) a polynucleotide encoding the Ssu72 peptide, or iii) an expression vector containing the polynucleotide in the manufacture of a medicament for alleviating or treating liver disease selected from the group consisting of non-alcoholic fatty liver, non-alcoholic steatohepatitis, and liver cirrhosis.

The pharmaceutical composition of the present invention may include a recombinant vector alone or one or more pharmaceutically acceptable carriers, which contains a pharmaceutically effective amount of Ssu72 peptide or a nucleotide encoding the Ssu72 peptide, or a vector comprising the polynucleotide as an active ingredient. In this case, pharmaceutically acceptable carriers may be those commonly used in formulation, and may include lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methylcellulose, methylhydroxybenzoate, propyl hydroxybenzoate, talc, magnesium stearate, and mineral oil. In addition, a lubricant, a wetting agent, a sweetening agent, a flavoring agent, an emulsifying agent, a suspending agent, a preservative, etc. may be additionally included in addition to the above components.

The composition according to an embodiment of the present invention may be administered by general systemic administration or topical administration, for example, intramuscular injection or intravenous injection, but when provided as a composition containing polynucleotide, intramuscular injection, subcutaneous injection, hydrodynamic injection, or the like, may be used when a viral vector is used. Otherwise, when a non-viral vector such as a plasmid vector is used, an electroporator may be used for the injection of DNA drugs into the body. Such electroporators include, for example, Glinporator™ of IGEA in Italy, CUY21EDIT of JCBIO in Korea, and SP-4a of Supertech in Switzerland.

The pharmaceutical composition according to an embodiment of the present invention may be administered through any general route as long as it can reach to target tissue. Such a route of administration may be parenteral administration, for example intraperitoneal administration, intravenous administration, intramuscular administration, subcutaneous administration, or intraperitoneal administration, but is not limited thereto.

The pharmaceutical composition according to an embodiment of the present invention may be formulated into a suitable form together with a generally used pharmaceutically acceptable carrier. Pharmacologically acceptable carriers may include, for example, water, suitable oil, saline, aqueous glucose, and a carrier for parenteral administration such as glycol, and may further include stabilizers and preservatives. Suitable stabilizers include antioxidants such as sodium hydrogen sulfite, sodium sulfite, or ascorbic acid. Suitable preservatives include benzalconium chloride, methyl- or propyl-parabene and chlorobutanol. In addition, the composition according to the present invention may appropriately include a suspension, a solubilizer, a stabilizer, an isotonic agent, a preservative, an adsorption inhibitor, a surfactant, a diluent, an excipient, a pH adjuster, a sedative-hypnotic agent, a buffer, an antioxidant, and the like, if necessary. Pharmacologically acceptable carriers and formulations suitable for the present invention, including those illustrated above, are described in detail in Remington's Pharmaceutical Sciences (latest edition).

The pharmaceutical composition of the present invention may be administered parenterally (e.g., intravenous, subcutaneous, intraperitoneal or topical) depending on the desired method, and the dosage may be appropriately selected by those skilled in the art although it may vary depending on the patient's condition and weight, degree of disease, drug form, route and duration of administration.

The pharmaceutical composition of the present invention is administered in a therapeutically effective amount. In the present invention, The "therapeutically effective amount" means an amount sufficient to treat a disease at a reasonable benefit/risk ratio applicable to medical treatment, and the therapeutically effective amount may vary according to the type and severity of the disease, drug activity, sensitivity to drugs, time of administration, route of administration and excretion rate of drugs, duration of treatment, factors including concomitant drugs, and other factors well known in the medical field. The pharmaceutical composition according to the present invention may be administered as an individual therapeutic agent or may be administered in combination with other therapeutic agents, may be administered sequentially or simultaneously with other conventional therapeutic agents, and may be administered as a single or multiple dose. Taking all of the above factors into consideration, it is important to administer an amount capable of obtaining the maximum effect with a minimum amount without side effects, which can be easily determined by those skilled in the art. Specifically, the therapeutically effective amount of the pharmaceutical composition of the present invention may vary depending on the age, sex, condition, weight of patients, absorption ratio of the active ingredient into the body, inactivation rate and excretion rate, disease type, and drugs used in combination, generally 1 to 500 mg per 1 kg of body weight may be administered daily or every other day, or divided into 1 to 3 times a day. However, since it may increase or decrease depending on the route of administration, sex, weight, age, etc., the dosage is not intended to limit the scope of the present invention in any way.

In a preferred embodiment, where the vector is an AAV vector, the dosage of the vector may be from $1 \times 10^{10}$ gc/kg to $1 \times 10^{15}$ gc/kg or more, suitably from $1 \times 10^{12}$ gc/kg to $1 \times 10^{14}$ gc/kg, suitably from $5 \times 10^{12}$ gc/kg to $5 \times 10^{13}$ gc/kg.

In general, the subject in need thereof will be a mammal, and preferably primate, more preferably a human. Typically, the subject in need thereof will display symptoms characteristic of a disease. The method typically comprises ameliorating the symptoms displayed by the subject in need thereof, by expressing the therapeutic amount of the therapeutic product.

Gene therapy protocols for therapeutic gene expression in target cells in vitro and in vivo, are well-known in the art and will not be discussed in detail herein. Briefly, they include intramuscular injection, interstitial injection, instillation in airways, application to endothelium, intra-hepatic injection, intra-parenchymal injection or intravenous or intra-arterial administration (e.g. intra-hepatic artery, intra-hepatic vein) of plasmid DNA vectors (naked or in liposomes) or viral vectors. Various devices have been developed for enhancing the availability of DNA to the target cell. While a simple approach is to contact the target cell physically with catheters or implantable materials containing the relevant vector, more complex approaches can use jet injection devices or electroporators for the intramuscular gene transfer. Gene transfer into mammalian liver cells has been performed using both ex vivo and in vivo procedures. The ex vivo approach typically requires harvesting of the liver cells, in vitro transduction with suitable expression vectors, followed by reintroduction of the transduced hepatocytes the liver. In vivo gene transfer has been achieved by injecting the non-viral vectors or viral vectors into the liver parenchyma, hepatic artery, or portal vein.

Non-alcoholic fatty liver is characterized by the accumulation of triglycerides in hepatocytes without excessive alcohol consumption. Non-alcoholic fatty liver continues to increase due to excessive nutrition associated with high-fat and high-carbohydrate intake in modern people. Non-alcoholic fatty liver is commonly observed in subjects suffering from obesity and diabetes, but various factors are known to be related to non-alcoholic fatty liver, and 80% of adults with non-alcoholic fatty liver are reported to develop metabolic syndromes such as insulin-resistant diabetes and heart disease. Pathologically, non-alcoholic fatty liver is classified as non-alcoholic simple steatosis and non-alcoholic steatohepatitis with inflammation, which can be transmitted to serious liver diseases such as hepatitis, liver fibrosis and cirrhosis when left unattended for a long time. Non-alcoholic fatty liver is characterized by having fat accumulation (fat infiltration) in hepatocytes and can progress to non-alcoholic steatohepatitis (NASH). Fat accumulation in non-alcoholic steatohepatitis is associated with various degrees of liver inflammation, and in many cases related to insulin resistance, dyslipidemia, and hypertension, and often occurs in subject with overweight, high cholesterol and triglyceride levels, or insulin resistance.

In addition, the incidence of non-alcoholic steatohepatitis is explained by the two-hit hypothesis, which initially results in fat accumulation in liver tissue, and then inflammatory reactions occur when fat accumulation in liver tissue worsens, resulting in fat peroxidation and deterioration of inflammation. Non-alcoholic steatohepatitis is known to be exacerbated by various causes such as hepatocellular necrosis, adiposis, lipotoxicity, and hepatitis caused by liver damage, and it is important to treat non-alcoholic steatohepatitis early before severe non-alcoholic steatohepatitis occurs. This is because treatment is very difficult in patients with non-alcoholic steatohepatitis with advanced liver fibrosis, or patient with liver fibrosis stage 3 and 4, which has also been proven in several clinical trials. Therefore, it is necessary to develop therapeutic agents for severe non-alcoholic steatohepatitis patients since it is difficult to treat severe non-alcoholic steatohepatitis patients with advanced liver fibrosis. Compared to the rapid increase in the number of non-alcoholic steatohepatitis patients, no excellent therapeutic agent for non-alcoholic steatohepatitis is reported yet. Due to the absence of therapeutic agents, other therapeutic agents for metabolic syndrome such as abdominal obesity, hyperlipidemia, and diabetes, including insulin resistance improvement drugs, antioxidants (e.g., vitamin C, E), therapeutic for dyslipidemia, and liver protection agents are prescribed as a therapeutic agent for treating NASH, but they are hard to be regarded as direct treatments for NASH. In addition, as the number of non-alcoholic steatohepatitis patients increases along with the increase in the obese population, the non-alcoholic steatohepatitis treatment market has developed into a huge market size, and much attention is focused on the development of therapeutics therefor.

Against this background, in order to solve the above problems, the inventors have confirmed that a composition including a polynucleotide encoding the Ssu72 peptide or the Ssu72 peptide is effective in preventing or treating non-alcoholic fatty liver and liver fibrosis. Accordingly, an object of the present invention is to provide a pharmaceutical composition for preventing or treating non-alcoholic steatohepatitis and liver fibrosis, comprising an Ssu72 peptide or a polynucleotide encoding the Ssu72 peptide as an active ingredient.

Specifically, the present inventors cloned a polynucleotide encoding the Ssu72 peptide and inserted a polynucleotide into pCMV vector after treating BamHI and XbaI restriction enzymes in order to construct pCMV.HA-Ssu72. In addition, the present inventors constructed AAV8.TBG.HA-Ssu72 viral vector (hereinafter referred to as "AAV8 Ssu72") by removing a polynucleotide encoding Cre from AAV.TBG.PI.Cre,rBG vector (Addgene, USA) and inserting a polynucleotide encoding HA-Ssu72 derived from the pCMV.HA—The Ssu72 peptide into the AAV.TBG.PI.Cre.rBG vector treated with ClaI and SalI restriction enzymes in order to construct a viral vector, AAV8 vector expressing Ssu72. Thereafter, the effect of relieving and treating non-alcoholic steatohepatitis was verified using the prepared vector. Specifically, non-alcoholic steatohepatitis was induced in mice by applying a methionine and chlorine-deficient (MCD) diet, a western+fructose diet including a high-fat, high-cholesterol and high-sugar, a CD+HF diet in which high-fat is added in choline-deficient diet, STAM diet in which high fat is added into mice administrated with Streptozotocin, and choline-deficient, L-amino acid-deficient high-fat diet (CDAHF). The present inventors verified therapeutic effect of the therapeutic vector pCMV.HA-Ssu72 for alleviating and treating induced non-alcoholic steatohepatitis in the experimental animals applied with MCD diet, confirmed therapeutic effect of therapeutic recombinant virus, AAV8 Ssu72 for alleviating induced non-alcoholic steatohepatitis and analyzed lesion of non-alcoholic steatohepatitis through morphological and histochemical analyses. In addition, it was confirmed that administration of AAV8 Ssu72 to mice applied with a CD+HF diet can alleviate and treat inflammatory symptoms of non-alcoholic steatohepatitis, and administration of AAV8 Ssu72 to mice STAM model was applied could improve non-alcoholic steatohepatitis and liver fibrosis, and it was confirmed that liver fibrosis mechanisms in the liver can be inhibited by administrating AAV8 Ssu72 to mice in which non-alcoholic steatohepatitis was induced through applying a STAM model.

EXAMPLES

Hereinafter, the present invention will be described in more detail through following examples. However, the present invention is not limited to the examples disclosed below, can be implemented in various different forms. The examples are provided in order to fully disclose the present invention and fully inform those of ordinary skill in the art the scope of the present invention.

Example 1: Experimental Preparation

All animal experiments used in the present invention were performed according to guidelines of Association for Assessment and Accreditation of Laboratory Animal Care International (AAALAC International) and Institute of Laboratory Animal Resources (ILAR) which were approved by the Institutional Animal Care and Use Committee of Sungkyunkwan University School of Medicine (SUSM).

Figure 1:
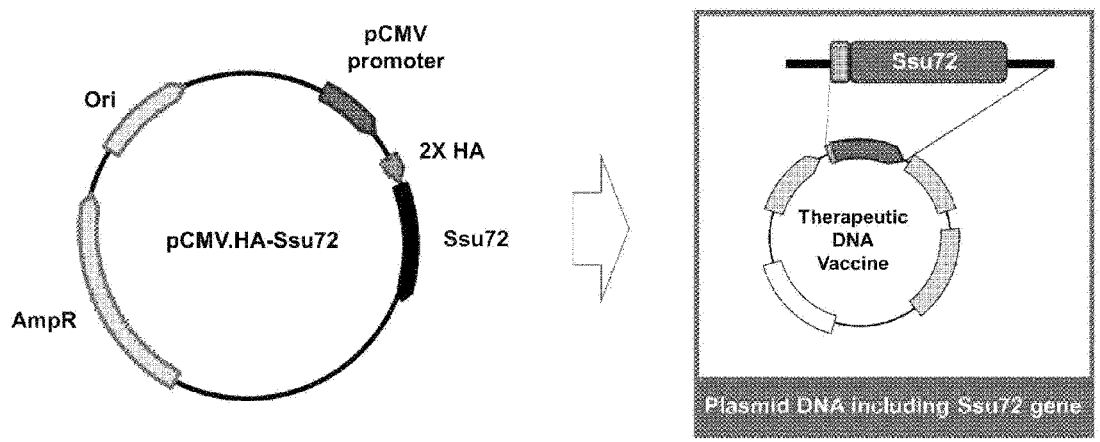

Example 2: Construction of Expression Vector Containing Polynucleotides Encoding Ssu72 Peptide 2-1: pCMV.HA-Ssu72 Plasmid Vector Construction The present inventors cloned the polynucleotide encoding Ssu72 (SEQ ID NO: 2) through PCR to construct a therapeutic non-viral pCMV vector expressing Ssu72, after treating the amplified polynucleotide with BamHI and XbaI restriction enzymes, and then inserting into the digested polynucleotide fragment into pCMV.HA vector (Clonetech, USA) and designated the constructed recombinant vector as "pCMV.HA-Ssu72" (FIG. 1).

2-2: AAV8.TBG.HA-Ssu72 (AAV8 Ssu72) Vector Construction

Figure 2:
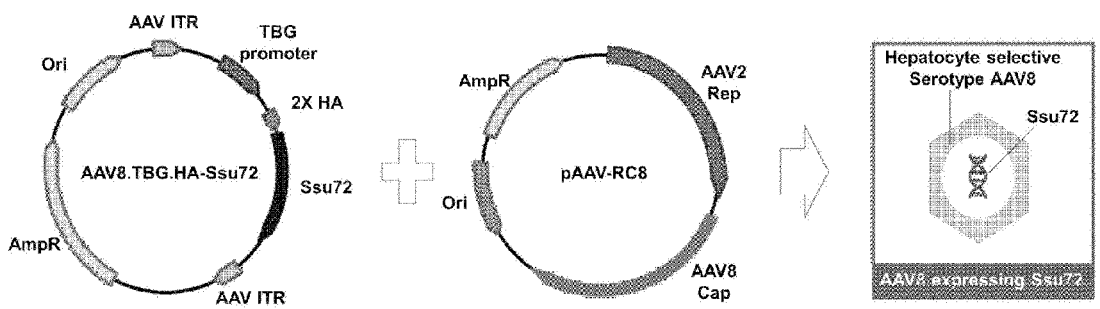

In order to construct an AAV8 vector expressing Ssu72, the present inventors transferred the polynucleotide encoding HA-Ssu72 excised from the pCMV.HA-Ssu72 vector prepared in Example 2-1 to the pAAV.TBG.PI.Cre.rBG vector (Addgene, USA) by removing a polynucleotide encoding Cre moiety form the pAAV.TBG.PI.Cre.rBG vector and inserting the excised polynucleotide to the pAAV.TBG.PI.Cre.rBG vector after digestion with ClaI and SalI restriction enzymes. The constructed vector was designated as "AAV8.TBG.HA-Ssu72 (AAV8 Ssu72)" (FIG. 2).

2-3: AAV8.TBG.HA-Ssu72 (AAV8 Ssu72) Virus Production

The present inventors prepared AAVs using the plasmid DNA obtained in Example 2-2. Specifically, to prepare the AAV, 293T cells were prepared the day before and stabilized for 24 hours, and the plasmid DNA prepared in Example 2-2 and pHelper and pAAV-RC8 (Agilent, USA), which are plasmids necessary for AAV production, added to the cells and the cells were transfected with the plasmids. The AAVs were obtained 3 to 4 days after transfection, and the prepared AAVs were quantified using a titration kit (AAVpro Titration Kit, Takara, Japan).

Example 3: Administration of Therapeutic Vector pCMV.HA-Ssu72

The present inventors verified therapeutic effect of pCMV.HA-Ssu72 which is a therapeutic vector according to an embodiment of the present invention for alleviating and treating non-alcoholic steatohepatitis induced by MCD diet. Particularly, an MCD diet was used to induce non-alcoholic steatohepatitis. First, after administrating the control vector and pCMV.HA-Ssu72 vector to the 6-week-old mice through the tail vein at a concentration of 5 µL/g, a non-alcoholic steatohepatitis diet was performed for 3 weeks. Thereafter, the collected liver was treated with formalin and paraffin, fixed liver was washed with 6 µm thick flakes, and hematoxylin and eosin (H&E) and oil red O staining were performed.

Figure 3A:
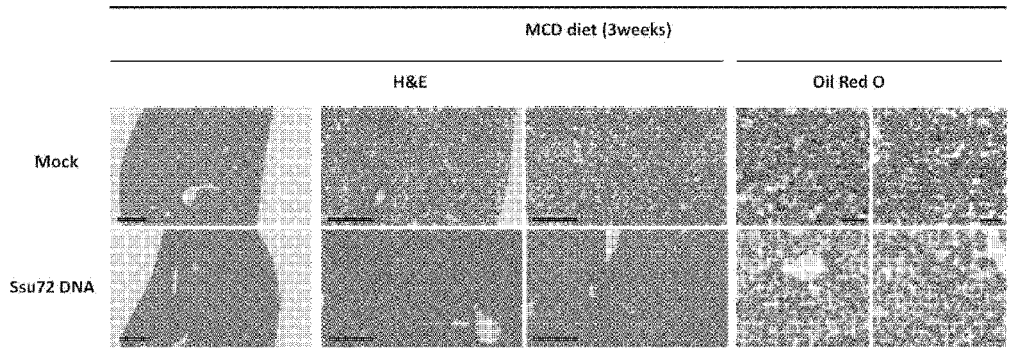
FIG. 3A is a series of microscopic photographs showing sections of liver tissues excised from experimental animals, stained with Oil Red O, representing a result of verifying the effectiveness of alleviating and treating liver disease of the therapeutic vector HA-Ssu72 according to an embodiment of the present invention following the induction of non-alcoholic steatohepatitis.
Figure 3B:
FIG. 3B is a graph showing the analysis of hepatic steatosis index (AST and ALT), representing a results of verifying the effectiveness of alleviating and treating liver diseases of the therapeutic vector HA-Ssu72 according to an embodiment of the present invention following the induction of non-alcoholic steatohepatitis.

As a result, non-alcoholic steatohepatitis was confirmed by accumulation of lipid droplets in the control group, but the experimental group of mice administered with the pCMV.HA-Ssu72 vector confirmed the alleviation and therapeutic effect of non-alcoholic steatohepatitis (FIG. 3A). In addition, as a result of comparing the levels of aspartate transaminase (AST) and alanine transferase (ALT) in serum, which can indirectly confirm the liver damage, it was found that the level decreased by more than 60% by administration of the pCMV.HA-Ssu72 vector (FIG. 3B). The above results suggest that Ssu72 expressed by the pCMV.HA-Ssu72 vector of the present invention improves or treats non-alcoholic steatohepatitis lesions.

Example 4: Administration of AAV8.TBG.HA-Ssu72 Viruses (AAV8 Ssu72)

The present inventors investigated the alleviating effect of AAV8 Ssu72 on non-alcoholic steatohepatitis after administration of AAV8.TBG.HA-Ssu72 viruses (AAV8 Ssu72). Specifically, the MCD diet was used to induce non-alcoholic steatohepatitis. Non-alcoholic steatohepatitis diet (MCD diet) for 2 weeks was applied after administering AAV8.GFP viruses (hereinafter abbreviated as 'AAV8') and AAV8 Ssu72 viruses to 6-week-old mice once in the tail vein at a concentration of $3 \times 10^{10}$ GC/g and the control group was subjected to a normal diet. Thereafter, livers of experimental mice were excised and photographed for efficacy evaluation, and the excised livers were treated with formalin and paraffin to fix them, and then H&E staining was performed.

As a result, there was no morphological or histological difference between AAV8 and AAV8 The Ssu72 peptide in the control group (FIG. 4A), but in the case of non-alcoholic steatohepatitis diet, in the liver of mice administered with AAV8, it was confirmed that the color of the liver was brightened to ocher which is a sign of lipid accumulation in the liver (FIG. 4B). In fact, as a result of H&E staining, in the experimental group administrated with control viruses, AAV8, accumulation of lipid droplets and ballooning of hepatocytes, which are known as an intrinsic characteristic of human NAFLD, were observed. On the other hand, in the case of non-alcoholic steatohepatitis diet after administration of AAV8 Ssu72, fat accumulation and infiltration of immune cells were significantly reduced, and hepatocyte ballooning was not observed at all. The above results suggest that Ssu72 expressed by administration of AAV8 Ssu72 of the present invention alleviates or treats non-alcoholic steatohepatitis lesions.

Example 5: Morphological and Histological Analysis of Liver

The present inventors performed morphological and histological analysis of the liver with non-alcoholic steatohepatitis lesions after administration of the AAV8.TBG.HA-Ssu72 viruses (AAV8 Ssu72) of the present invention. Specifically, in order to investigate whether the increase in Ssu72 peptide expression in the liver caused by administration of AAV8 Ssu72 ($3 \times 10^{10}$ GC/g) causes changes in the morphological and histological environment of the actual non-alcoholic steatohepatitis, and thereby can alleviate the level of adiposis and lipotoxicity, infiltration of immune cells, hepatic fibrosis level, Oil red O staining were performed. At this time, the control group was analyzed as a group administered with AAV8.

As a result, immunostaining confirmed Ssu72 expressed in hepatocytes through the anti-HA antibodies, and Oil red O staining showed that the accumulation of lipid droplets in the liver of mice decreased after administration of AAV8 Ssu72 (FIG. 5A). In addition, it was confirmed that non-alcoholic steatohepatitis was improved to the extent that SMA, a marker of liver fibrosis, was hardly observed (FIG. 5B).

Example 6: Verification of the Role of the Ssu72 Gene

The present inventors verified the role of the Ssu72 gene by a non-alcoholic steatohepatitis induction diet using transgenic mice in which liver-specific Ssu72 expression is suppressed. Specifically, the effect of suppression of Ssu72 expression on the onset and progression of non-alcoholic steatohepatitis was confirmed through Western+Fructose diet using normal mice and the transgenic mice whose expression of The Ssu72 peptide in the liver is suppressed. Western+Fructose diet was applied to a normal mouse group and a transgenic mouse group in which liver-specific Ssu72 expression was suppressed, and 3 months later, the livers of the mice were excised and H&E staining and Sirius red staining were performed.

As a result, increase in the level of steatosis in the liver tissue and in the invasiveness of immune cells were observed through H&E staining, and it was confirmed that the progression of non-alcoholic steatohepatitis was significantly accelerated in the transgenic mouse group in which the expression of Ssu72 was suppressed specifically in the liver and it was observed that the progress of liver fibrosis became severe through Sirius red staining (FIG. 6).

Example 7: Confirmation of Treatment Effect for Non-Alcoholic Steatohepatitis 7-1: Sirius Red Staining and Immunostaining The present inventors investigated the alleviation and therapeutic effect of AAV8.TBG.HA-Ssu72 virus (AAV8 Ssu72) on non-alcoholic steatohepatitis using Choline-deficient+High fat (CD+HFD). Specifically, to confirm the therapeutic effect of Ssu72 of the present invention for non-alcoholic steatohepatitis, Choline-deficient+High fat diet (CD+HF diet), which is another non-alcoholic steatohepatitis diet, was applied to mice, after administration of AAV8 Ssu72 to mice ($2 \times 10^{10}$ GC/g). The therapeutic effect of AAV8 Ssu72 was verified through Sirius red staining and immunostaining.

As a result, a single administration of AAV8 Ssu72 showed a significant inhibitory effect on liver fibrosis compared to the AAV8 control group. This is considered to be the effect of lowering the fibrosis stage a step from the fibrosis stage 2 to the lower fibrosis stage 1. In addition, in order to closely measure the degree of infiltrating macrophages, the amount of inflammatory macrophages infiltrating the liver was measured using anti-Ly6c and anti-CD11b antibodies while non-alcoholic steatohepatitis was induced. It was shown that the inflammatory response was significantly reduced by the administration of AAV Ssu72 of the present invention (FIG. 7A). The amount of inflammatory macrophages infiltrating the liver was quantified based on the amount of foci formation. Ly6c$^+$, CD11b$^+$ macrophage quantification process was performed after immunostaining with Ly6c (green) and CD11b (red). Among the clusters of cells in which both proteins were expressed and appear yellow, the foci were set as that the size of the cells was 10 mm or more and the number of cells was 5 or more. In particular, except for clusters around blood vessels or bile ducts, the staining intensity should be above the basal level. After measuring and comparing the amount of foci formed by macrophages in the control group and the experimental group administered with AAV8 Ssu72, the amount of foci decreased in the experimental group administered with AAV8 Ssu72, showing a statistically significant difference (FIG. 7B).

7-1: RT-PCR

The present inventors obtained each total RNA according to the manual of the RNeasy Mini kit (Qiagen) after feeding the Choline-deficient+High fat Diet (CD+HF Diet) to mice, and then excising the liver tissues. Oligo primer was added to the obtained total RNA and pre-incubation was performed for 5 minutes at 70° C., followed by addition of a mixture of reverse transcriptase, RNase inhibitor, 25 mM $MgCl_2$ and dNTP, RT-PCR under the condition of 42° C. for 60 minutes, 85° C. for 5 minutes was performed to obtain cDNA from the total RNA. Real-time PCR was performed using the obtained cDNA and the following primers, and the expression levels of liver fibrosis-related genes, which are the most important indicators of non-alcoholic steatohepatitis treatment, were compared.

One of the main symptoms of non-alcoholic steatohepatitis is that hepatic stellate cells which exist in a quiescent stage in the normal liver are activated by lipotoxicity and various cytokines including TGF-β, and furthermore, the liver fibrosis occurs by degeneration of hepatic stellate cells into fibrous cells. However, the introduction of The Ssu72 peptide into the liver through the administration of AAV8 Ssu72 of the present invention significantly reduced the expression of TGF-β and Col1a1 genes, which are indicators of fibrosis, by 50% in the state of non-alcoholic steatohepatitis (FIG. 7C). The nucleotide sequence information of the above primers used in the present invention, including the detection of the liver fibrosis-related gene, is summarized in Table 1 below.

TABLE 1

| Nucleotide sequence information of primers | | |
|---|---|---|
| Primer | Nucleotide sequences (5' --> 3') | SEQ ID NOs: |
| TGF F | CACCGGAGAGCCCTGGATA | 5 |
| TGF R | TGTACAGCTGCCGCACACA | 6 |
| Col1a1 F | GGGTCTAGACATGTTCAGCTTTGTG | 7 |
| Col1a1 R | ACCCTTAGGCCATTGTGTATGC | 8 |
| Fasn F | ATTGCATCAAGCAAGTGCAG | 9 |
| Fasn R | GAGCCGTCAAACAGGAAAG | 10 |
| Srebp1c F | GGCTTGTCCTTTGGGAAGC | 11 |
| Srebp1c R | CGCCTATGCTGGTGCACA | 12 |
| ACC1 F | CCAGGCCATGTTGAGACGCT | 13 |
| ACC1 R | CCAGCCAGCCTCTTGACTAT | 14 |
| PPARa F | GGATGTCACACAATGCAATTCG | 15 |
| PPARa R | TCACAGAACGGCTTCCTCAGGT | 16 |

TABLE 1-continued

Nucleotide sequence information of primers

| Primer | Nucleotide sequences (5' --> 3') | SEQ ID NOs: |
|---|---|---|
| Pgc1a F | CCCTGCCATTGTTAAGACC | 17 |
| Pgc1a R | TGCTGCTGTTCCTGTTTTC | 18 |
| Col3a1 F | TACACCTGCTCCTGTGCTTC | 19 |
| Col3a1 R | CATTCCTCCCACTCCAGACT | 20 |
| MMP12 F | ACCAGAGCCACACTATCCC | 21 |
| MMP12 R | CTCCTGCCTCACATCATACC | 22 |
| MMP13 F | CTGGCACACGCTTTTCCTC | 23 |
| MMP13 R | ATGGGCAGCAACAATAAACAAG | 24 |
| SMA F | CTGACAGAGGCACCACTGAA | 25 |
| SMA R | CATCTCCAGAGTCCAGCACA | 26 |
| Timp F | CTCAAAGACCTATAGTGCTGGC | 27 |
| Timp R | CAAAGTGACGGCTCTGGTAG | 28 |

Example 8: Real-Time qRT-PCR Analysis Using Liver Tissues

The present inventors administered the AAV8.GFP viruses (AAV8) and AAV8.TBG.HA-Ssu72 viruses (AAV8 Ssu72) of the present invention to mice, and fed a normal or non-alcoholic steatohepatitis diet (MCD diet) for 2-3 weeks and then the liver tissues were excised from the mice. Total RNA was obtained from the excised liver tissues according to the manual of RNeasy Mini kit (Qiagen). Oligo primer was added to the obtained total RNA and pre-incubation was performed for 5 minutes at 70° C., followed by addition of a mixture of reverse transcriptase, RNase inhibitor, 25 mM $MgCl_2$ and dNTP, RT-PCR under the condition of 42° C. for 60 minutes, 85° C. for 5 minutes was performed to obtain cDNA from the total RNA. Real-time PCR was performed using the obtained cDNA and the above-described primers, and the expression levels of lipogenesis, lipid metabolism, and fibrosis-related genes expressed in the liver were compared.

As a result, regardless of the diet, by the expression of The Ssu72 peptide in the liver, the expression of Fasn, Srebp1c and ACC1 involved in adipogenesis were decreased, and a marked suppression of adipogenesis was observed in the nonalcoholic steatohepatitis diet. In contrast, the expression of fat metabolism and degradation-related genes {PPARα (peroxisome proliferator-activated receptor alpha), PGC1α (peroxisome proliferator-activated receptor gamma coactivator 1-alpha)} was increased by Ssu72 expression (FIG. 8a). These results suggest that the expression of The Ssu72 peptide increases the function and mitochondrial activity in liver cells. In addition, based on the above results, after liver excision under the same conditions, western blot and immunostaining of proteins related to adipogenesis and fat metabolism were performed. As a result, the expression of fat metabolism-related proteins PPARα and PGC1α increased, and the expression of ChREBP, which is a key transcription factor for de novo lipogenesis, was significantly reduced after administration of AAV8 Ssu72 viruses (FIGS. 8b and 8c). The ChREBP, a key factor in de nove adipogenesis according to glucose influx from the liver, is actually a regulator of insulin sensitivity and insulin resistance in the liver (Mi-sung Kim et al., J. Clin. Invest. 126(11): 4372-4386. 2016). In addition, it was confirmed that hepatic and peripheral insulin sensitivity was restored when the liver-specific ChREBP was inhibited in insulin-resistant mice (Tara Jois et al., Mol. Metab. 6(11): 1381-1394. 2017). Therefore, from the immunostaining analysis it was confirmed that ChREBP expression was significantly suppressed after AAV8 Ssu72 administration in mice with non-alcoholic steatohepatitis, suggesting that the results are related to the reduction of de novo adipogenesis in the liver and the restoration of insulin resistance.

Example 9: Comparison of Formation of Reactive Oxygen Species (ROS) and Abnormal Metabolites (e.g. 4-HNE)

The present inventors compared the formation of ROS and abnormal metabolites, 4-HNE (4-hydroxynonenal), in non-alcoholic steatohepatitis liver tissue after administration of AAV8.TBG.HA-Ssu72 viruses (AAV8 Ssu72). Specifically, it is known that non-alcoholic steatohepatitis is induced by abnormal metabolites such as 4-HNE generated during excessive influx of reactive oxygen species (ROS) into the liver or lipid peroxidation of the synthesized fatty acids. Accordingly, the present inventors compared the formation of ROS and the abnormal metabolite (4-HNE) in the non-alcoholic steatohepatitic liver tissues after administration of AAV8 Ssu72 viruses ($3\times10^{10}$ GC/g) using AAV8.GFP viruses (AAV8) as a control.

As a result, it was found that 4-HNE was excessively produced in the transgenic mice in which the liver-specific expression of Ssu72 was suppressed (FIG. 9A). The 4-HNE is produced during the oxidation process of fatty acids in mitochondria or peroxisomes, and acts as an adduct to DNA and proteins, and induces abnormal regulation or apoptosis of hepatocytes. In addition, it acts as a major factor causing fibrosis by inducing the activation of hepatic stellate cells in non-alcoholic steatohepatitis lesions. The present inventors administered AAV8 Ssu72 viruses to mice, followed by feeding a normal or nonalcoholic steatohepatitis diet (MCD diet) for 2 weeks, and then liver tissues was excised from mice and western blot was performed. As a result, in the group administered with AAV8 Ssu72 viruses, it was found that the protein adduct of 4-HNE was significantly reduced (FIG. 9B). The above results suggest that the expressed Ssu72 is effective in alleviating and treating non-alcoholic steatohepatitis by inhibiting abnormal regulation or apoptosis of hepatocytes.

Example 10: Confirmation of Inhibition of Liver Fibrosis Mechanism

The present inventors investigated the inhibition of the liver fibrosis mechanism in non-alcoholic steatohepatitic liver tissue after administration of the AAV8.TBG.HA-Ssu72 viruses (AAV8 Ssu72) of the present invention. One of the main symptoms of non-alcoholic steatohepatitis is that hepatic stellate cells which exist in a quiescent stage in the normal liver are activated by lipotoxicity and various cytokines including TGF-β, and furthermore, the liver fibrosis occurs by degeneration of hepatic stellate cells into fibrous cells. Accordingly, the present inventors investigated whether mechanism of hepatic fibrosis can be inhibited in the non-alcoholic steatohepatitic liver tissues after administration of AAV8 Ssu72 viruses ($3\times10^{10}$ GC/g) using AAV8.GFP viruses (AAV8) as a control using real time PCR (See Table 1) and western blot analysis.

As a result, the introduction of The Ssu72 peptide into the liver through the administration of AAV8 Ssu72 significantly reduced the expression of TGF-β, Col1a1, and Col3a1 genes, which are indicators of fibrosis in non-alcoholic steatohepatitis, and the expression of the MMP12 gene that degrades collagen was significantly increased (FIG. 10A). In addition, as a result of confirming the expression level of TGF-β in the actual liver tissue by western blot, it was found that the AAV8 Ssu72 was significantly inhibited the level of TGF-β (FIG. 10B). Therefore, taking the above results together, the induction of Ssu72 expression in the liver using AAV inhibited hepatocyte damage caused by lipotoxicity, reduced histological defects accompanied by infiltration of inflammatory cells, and remarkably reduced the level of liver fibrosis. Therefore, it suggests that Ssu72 peptide or a polynucleotide encoding the same can be used as an excellent therapeutic agent for the prevention and treatment of non-alcoholic steatohepatitis.

Example 11: Confirmation of Therapeutic Effect of AAV8 Ssu72 on Non-Alcoholic Steatohepatitis and Liver Fibrosis Using STAM Model The present inventors investigated the therapeutic effect of AAV8.TBG.HA-Ssu72 virus (AAV8 Ssu72) on nonalcoholic steatohepatitis and liver fibrosis using the STAM model. Specifically, streptozotocin (STZ) was administered to 2-day-old mice, and non-alcoholic steatohepatitis was induced by feeding a high-fat diet from 4 weeks of age to 12 weeks of age. The mice were induced to develop fatty liver at 6 weeks of age, non-alcoholic steatohepatitis at 8 weeks of age, and cirrhosis at 12 weeks of age. After confirming that non-alcoholic steatohepatitis and liver fibrosis were induced at 8 weeks of age, AAV8 Ssu72 was administered ($3\times10^{10}$ GC/g) to the mice and liver tissues excised at 12 weeks of age were stained with H&E and indicators capable of determining degree of non-alcoholic steatohepatitis and hepatic fibrosis were analyzed (FIG. 11A). At this time, the control group was administered with AAV8.GFP viruses (AAV8).

As a result, it was confirmed that fat accumulation, hepatocyte ballooning, and immune cell infiltration were improved to a normal liver state in the group administered with AAV8 Ssu72 compared to the control group (FIG. 11B). In addition, administration of AAV8 Ssu72 significantly improved the degree of steatosis, lobular inflammation, and ballooning of hepatocytes, indicating that NAFLD activity was significantly reduced compared to the control group administered with AAV8. In particular, in the group administered with AAV8 Ssu72, the degree of inflammation was improved to the point that almost no inflammation was observed, and indicators of liver function (AST, ALT) were also reduced. (FIG. 11C).

Example 12: Confirmation of the Therapeutic Effect of AAV8 Ssu72 on Nonalcoholic Steatohepatitis and Liver Fibrosis Using the CDAHFD Model The present inventors investigated the therapeutic effect of AAV8.TBG.HA-Ssu72 virus (AAV8 Ssu72) on nonalcoholic steatohepatitis and liver fibrosis using the CDAHFD model. Specifically, in a model in which CDAHFD diet was fed to mice for about 11 weeks to induce non-alcoholic steatohepatitis and liver fibrosis, and then changed to a high-fat diet for 3 weeks and continued fat accumulation in the liver, after administration of AAV8 Ssu72, H&E staining and Sirius red staining was performed. At this time, AAV8 Ssu72 was administered as a single dose ($3\times10^{10}$ GC/g) on the $11^{th}$ week from the start of the CDAHF diet, and was changed to a high-fat diet 3 days before administration of AAV8 Ssu72 (FIG. 12A). At this time, the control group was administered with AAV8.GFP viruses (AAV8).

As a result, it was observed that the level of steatosis, the infiltration of immune cells, and the progress of liver fibrosis were all improved to a normal liver state in the group administered with AAV8 Ssu72 compared to the control group (FIG. 12B). In addition, through the administration of AAV8 Ssu72, the level of the fibrosis marker that can confirm the expression level of disease marker genes of liver fibrosis and fibrosis markers capable of determining the degree of alleviation of fibrosis and the level of the enzyme inhibiting the fibrosis were confirmed by qRT-PCT (see Table 1). As a result, it was confirmed that the level of MMP13 which is an indicator of suppression of fibrosis was increased by about 4 times compared to the control group by the administration of AAV8 Ssu72, but the expression levels of TGF-β, Col1a1, SMA, Timp1 gene, which are indicators for liver fibrosis were decreased by about 50% (FIG. 12C).

In conclusion, the pharmaceutical composition for preventing or treating liver disease comprising the Ssu72 peptide or a polynucleotide encoding the Ssu72 peptide of the present invention can effectively inhibit the lipogenesis activity of hepatocytes, inhibit the activation and invasion of various immune cells, including macrophages through inhibition of hepatocellular adipogenesis and inhibit the activation and fibrosis of hepatic stellate cells by inhibiting expression and secretion of TGF-β. Thus, the pharmaceutical composition can be used as a therapeutic agent that can very effectively prevent and treat non-alcoholic fatty liver, non-alcoholic steatohepatitis, and liver fibrosis.

Although the present invention has been described with reference to the above-described examples, these are merely exemplary, and those skilled in the art will understand that various modifications and equivalent other embodiments are possible therefrom. Therefore, the true scope of the present invention should be determined by the technical features of the appended claims.

INDUSTRIAL APPLICABILITY

The present invention is drawn to a pharmaceutical composition for treating liver disease. Particularly, the present invention can be used for manufacturing therapeutic agents, especially therapeutic agents for treating liver diseases such as fatty liver, non-alcoholic steatohepatitis and liver cirrhosis.

The present invention was developed during the research on the deduction of drug candidate substances for gene therapy for treating nonalcoholic steatohepatitis in the national new drug development project (Project ID No.: 1465034859, Project No.: HN21C0805000021, Project period: 2021.09.01-2023.08.31), which is a research project supported by multiple ministries of Korean government and the Korea Health Industry Promotion Agency, and executed by one of the present applicant, CUROGEN Technology, Co. Ltd.

The invention claimed is:

1. A method for treating a patient suffering from a liver disease selected from the group consisting of non-alcoholic fatty liver, non-alcoholic steatohepatitis and hepatic fibrosis comprising administrating via systemic administration or intra-hepatic injection to the patient at least one selected from the group consisting of a Ssu72 peptide, a polynucleotide encoding the Ssu72 peptide, and an expression vector comprising the polynucleotide,
wherein the polynucleotide is operably linked to a promoter, and
wherein the patient shows lower expression or activity of Ssu72 peptide in the liver than a normal subject.

2. The method according to claim 1, wherein the Ssu72 peptide has the amino acid sequence represented by SEQ ID NO: 1.

3. The method according to claim 2, wherein the Ssu72 peptide is encoded by a polynucleotide having the nucleotide sequence represented by SEQ ID NO: 2.

4. The method according to claim 1, wherein the polynucleotide is DNA.

5. The method according to claim 1, wherein the expression vector is a viral vector.

6. The method according to claim 5, wherein the viral vector is an adeno-associated virus (AAV) vector, an adenovirus vector, an alphavirus vector, a herpes simplex virus vector, a vaccinia virus vector, a Sendai virus vector, a flavivirus vector, a radovirus vector, a retroviral vector, a herpesvirus vector, a poxvirus vector or a lentiviral vector.

7. The method according to claim 6, wherein the viral vector is an adeno-associated virus (AAV) vector.

8. The method according to claim 7, wherein the AAV vector is an AAV8 vector.

9. The method according to claim 1, wherein the promoter is constitutive promoter, an inducible promoter, or a liver-specific promoter.

10. The method according to claim 9, wherein the constitutive promoter is a CMV promoter.

11. The method according to claim 9, the liver-specific promoter is a thyroxin-binding globulin (TBG) promoter, a PBGD promoter, an α-1 anti-trypsin promoter (EhAlbAAT), a Hepatic Control Region (HCR)-ApoCII hybrid promoter, an HCR-hAAT hybrid promoter, an apolipoprotein E (ApoE) promoter, a phosphoglycerate kinase (PGK) promoter, or a hybrid liver-specific promoter (HLP).

12. The method according to claim 11, the liver-specific promoter comprises the nucleotide sequence represented by SEQ ID NO: 3.

13. The method according to claim 9, wherein the constitutive promoter is a CMV promoter.

14. A method for preventing a liver disease selected from the group consisting of non-alcoholic fatty liver, non-alcoholic steatohepatitis and hepatic fibrosis, comprising administering at least one selected from the group consisting of i) to iii) to a subject in need thereof, via systemic administration or intra-hepatic injection:
i) an Ssu72 peptide having an amino acid sequence represented by SEQ ID NO: 1,
ii) a polynucleotide encoding the Ssu72 peptide, and
iii) an expression vector containing the polynucleotide,
wherein the polynucleotide is operably linked to a promoter, and
wherein the subject shows lower expression or activity of Ssu72 peptide in the liver than a normal subject.

15. The method according to claim 14, wherein the polynucleotide is DNA.

16. The method according to claim 14, wherein the Ssu72 peptide is encoded by a polynucleotide having the nucleotide sequence represented by SEQ ID NO: 2.

17. The method according to claim 14, wherein the expression vector is a viral vector.

18. The method according to claim 17, wherein the viral vector is an adeno-associated virus (AAV) vector, an adenovirus vector, an alphavirus vector, a herpes simplex virus vector, a vaccinia virus vector, a Sendai virus vector, a flavivirus vector, a radovirus vector, a retroviral vector, a herpesvirus vector, a poxvirus vector or a lentiviral vector.

19. The method according to claim 17, wherein the viral vector is an adeno-associated virus (AAV) vector.

20. The method according to claim 19, wherein the AAV vector is an AAV8 vector.

21. The method according to claim 14, wherein the promoter is a constitutive promoter, or a liver-specific promoter.

22. The method according to claim 21, wherein the liver-specific promoter is a thyroxin-binding globulin (TBG) promoter, a PBGD promoter, an a-1 anti-trypsin promoter (EhAlbAAT), an Hepatic Control Region (HCR)-ApoCII hybrid promoter, an HCR-hAAT hybrid promoter, an apolipoprotein E (ApoE) promoter, a phosphoglycerate kinase [PGK] promoter, and a hybrid liver-specific promoter (HLP).

23. The method according to claim 22, wherein the TBG promoter comprises the nucleotide sequence represented by SEQ ID NO: 3.

24. The method according to claim 21, wherein the constitutive promoter is a CMV promoter.

* * * * *